(12) United States Patent
Choi et al.

(10) Patent No.: US 12,317,743 B2
(45) Date of Patent: May 27, 2025

(54) N-TYPE SEMICONDUCTOR, AND ORGANIC PHOTOELECTRIC DEVICE, IMAGE SENSOR, AND ELECTRONIC DEVICE INCLUDING THE SAME

(71) Applicants: Samsung Electronics Co., Ltd., Suwon-si (KR); SEOUL NATIONAL UNIVERSITY R&DB FOUNDATION, Seoul (KR)

(72) Inventors: Yeong Suk Choi, Suwon-si (KR); Soo Young Park, Seoul (KR); Sung Young Yun, Suwon-si (KR); Hyeong-Ju Kim, Changwon-si (KR); Seyoung Jung, Busan (KR); Dong Joo Min, Seoul (KR); Ji Eon Kwon, Seoul (KR)

(73) Assignees: Samsung Electronics Co., Ltd., Gyeonggi-do (KR); Seoul National University R&DB Foundation, Seoul (KR)

( * ) Notice: Subject to any disclaimer, the term of this patent is extended or adjusted under 35 U.S.C. 154(b) by 160 days.

(21) Appl. No.: 18/344,265

(22) Filed: Jun. 29, 2023

(65) Prior Publication Data
US 2023/0345823 A1 Oct. 26, 2023

Related U.S. Application Data

(62) Division of application No. 17/092,399, filed on Nov. 9, 2020, now Pat. No. 11,737,359.

(30) Foreign Application Priority Data

Nov. 7, 2019 (KR) .......................... 10-2019-0141795

(51) Int. Cl.
*H10K 85/60* (2023.01)
*C07C 255/35* (2006.01)
(Continued)

(52) U.S. Cl.
CPC ......... *H10K 85/654* (2023.02); *C07C 255/35* (2013.01); *C07D 213/57* (2013.01);
(Continued)

(58) Field of Classification Search
None
See application file for complete search history.

(56) References Cited

U.S. PATENT DOCUMENTS 8,525,577 B2 9/2013 Yofu et al.
10,263,194 B2 4/2019 Seo et al.
(Continued)

FOREIGN PATENT DOCUMENTS

JP 2010079291 A 4/2010
KR 2016/0134501 A 11/2016
WO WO-2016025430 A1 2/2016

OTHER PUBLICATIONS

Korean Office Action dated Aug. 14, 2024 for corresponding Korean Patent Application No. 10-2019-0141795 and its English-language translation.
(Continued)

*Primary Examiner* — Anthony Ho
(74) *Attorney, Agent, or Firm* — HARNESS, DICKEY & PIERCE, P.L.C.

(57) ABSTRACT

Disclosed are an n-type semiconductor including compound represented by Chemical Formula 1 or Chemical Formula 2, an image sensor, and an electronic device.

(Continued)

[Chemical Formula 1]

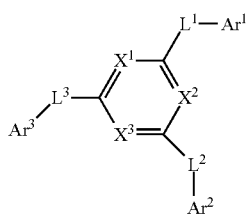

[Chemical Formula 2]

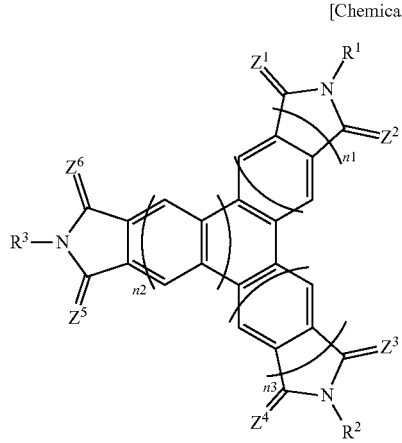

In Chemical Formula 1 and Chemical Formula 2, each substituent is as defined in the detailed description.

6 Claims, 8 Drawing Sheets

(51) Int. Cl.
| | |
|---|---|
| *C07D 213/57* | (2006.01) |
| *C07D 401/14* | (2006.01) |
| *C07D 487/14* | (2006.01) |
| *H10K 85/20* | (2023.01) |
| *H10K 30/30* | (2023.01) |
| *H10K 39/32* | (2023.01) |

(52) U.S. Cl.
CPC ......... *C07D 401/14* (2013.01); *C07D 487/14* (2013.01); *H10K 85/211* (2023.02); *H10K 85/60* (2023.02); *H10K 85/6572* (2023.02); *H10K 30/30* (2023.02); *H10K 39/32* (2023.02)

(56) References Cited

U.S. PATENT DOCUMENTS 11,088,335 B2   8/2021   Seo et al.
11,889,759 B2   1/2024   Seo et al.

OTHER PUBLICATIONS

Ali Yassin et al., 'Structure-Thermodynamic-Property Relationships in Cyanovinyl-Based Microporous Polymer Networks for the Future of Design of Advanced Carbon Capture Materials' *Advanced Functional Materials*, 2017, 27, 1700233.

Yoonbin Lim et al., 'Constitutional isomers of a C3-symmetric molecule showing different piezochromic behaviours: on-off switching and colour tuning' *Journal of Materials Chemistry C*, 2014, 2, pp. 5963-5968.

Afef Béjaoui et al., 'Chemical composition and bioactivities of the polyphenolic-rich extract of *Ormenis africana* Jord. and Fourr' *International Journal of Food Properties*, 2017, vol. 20, No. 8, pp. 1786-1795.

Hokuto Seo et al., 'Color Sensors with Three Vertically Stacked Organic Photodetectors' *Japanese Journal of Applied Physics*, vol. 46, No. 49, 2007, pp. L1240-L1242.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

Mikio Ihama et al., 'CMOS Image Sensor with a Thin Overlaid Panchromatic Organic Photoconductive Layer for Sensors with Reduced Pixel Size' *IDW* '09, 2009, pp. 2123-2126.

Seon-Jeong Lim et al., 'Organic-on-silicon complementary metal-oxide-semiconductor colour image sensors' *Scientific Reports*, 5:7708, Jan. 2015.

D. V. Konarev et al., 'Donor-acceptor interaction of fullerene $C_{60}$ with triptycene in molecular complex TPC $C_{60}$' *Journal of Molecular Structure*, 526, 2000, pp. 25-29.

N-TYPE SEMICONDUCTOR, AND ORGANIC PHOTOELECTRIC DEVICE, IMAGE SENSOR, AND ELECTRONIC DEVICE INCLUDING THE SAME

CROSS-REFERENCE TO RELATED APPLICATION

This application is a divisional of U.S. application Ser. No. 17/092,399, filed Nov. 9, 2020, which claims priority to and the benefit of Korean Patent Application No. 10-2019-0141795 filed in the Korean Intellectual Property Office on Nov. 7, 2019, the entire contents of each of which are incorporated herein by reference.

BACKGROUND

1. Field

Example embodiments provide an n-type semiconductor and an organic photoelectric device, an image sensor, and an electronic device including the same.

2. Description of the Related Art

Fullerene is a closed-cage molecule made of carbon and is used in various fields because of its stable structure and good electrical properties.

An organic photoelectric device is a device that converts light into an electrical signal using a photoelectric effect. The organic photoelectric device includes a photodiode and a phototransistor, and may be applied to an electronic device such as an image sensor. The organic photoelectric device may include fullerene in the active layer having high light absorption properties and good electrical properties.

However, fullerene may absorb light in a blue region (about 450 nm region) and reduce color clarity of the organic photoelectric device to which the fullerene is applied.

Therefore, development of an n-type semiconductor that does not exhibit absorption in the blue region has been requested.

SUMMARY

Example embodiments provide an n-type semiconductor capable of improving the color clarity of the organic photoelectric device by reducing the absorption of the blue region and having excellent heat resistance.

Example embodiments also provide a thin film and an organic photoelectric device including the n-type semiconductor.

Example embodiments also provide an image sensor and an electronic device including the organic photoelectric device.

According to example embodiments, an n-type semiconductor including a compound represented by Chemical Formula 1 is provided.

[Chemical Formula 1]

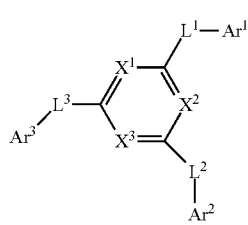

In Chemical Formula 1, $X^1$, $X^2$, and $X^3$ are $CR^a$ or N, (wherein $R^a$ is hydrogen, deuterium, a halogen, a C1 to C10 alkyl group, a C1 to C10 haloalkyl group, a C6 to C10 aryl group, or a C2 to C10 heteroaryl group), $L^1$, $L^2$, and $L^3$ are independently a single bond, a substituted or unsubstituted C1 to C30 alkylene group, a substituted or unsubstituted C2 to C30 alkenylene group, a substituted or unsubstituted C2 to C30 alkynylene group, or a substituted or unsubstituted C1 to C30 alkylene group, a substituted or unsubstituted C2 to C30 alkenylene group, or a substituted or unsubstituted C2 to C30 alkynylene group that includes at least one linker selected from —$NR^b$—, —C(=O)—, —S(=O)—, —OC(=O)—, —C(=O)O—, —S(=O)$_2$—, —Si($R^cR^d$)$_2$—, and —C(=O)$NR^e$— (wherein $R^b$, $R^c$, $R^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), and $Ar^1$, $Ar^2$, and $Ar^3$ are independently a C2 to C30 N-containing heteroaryl group, a C6 to C30 aryl group having at least one electron withdrawing functional group (EWG), or a C2 to C30 heteroaryl group having at least one electron withdrawing functional group.

In example embodiments, in Chemical Formula 1, $L^1$, $L^2$, and $L^3$ may independently be a C1 to C30 alkylene group substituted with an electron withdrawing functional group, a C2 to C30 alkenylene group substituted with an electron withdrawing functional group, or a C2 to C30 alkynylene group substituted with an electron withdrawing functional group.

In example embodiments, the compound represented by Chemical Formula 1 may be a compound represented by Chemical Formula 1-1 or 1-2.

[Chemical Formula 1-1]

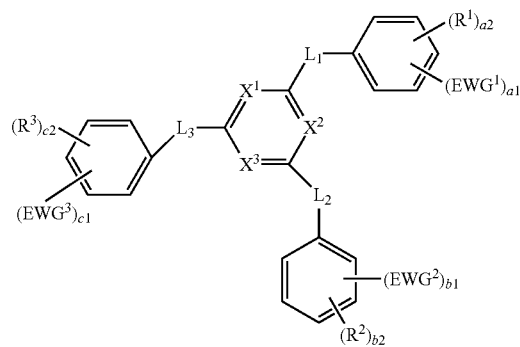

In Chemical Formula 1-1, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $L^1$, $L^2$, and $L^3$ are independently a single bond, a substituted or unsubstituted C1 to C30 alkylene group, a substituted or unsubstituted C2 to C30 alkenylene group, a substituted or unsubstituted C2 to C30 alkynylene group, or a substituted or unsubstituted C1 to C30 alkylene group, a substituted or unsubstituted C2 to C30 alkenylene group, or a substituted or unsubstituted C2 to C30 alkynylene group that includes at least one linker selected from —$NR^b$—, —C(=O)—, —S(═O)—, —OC(═O)—, —C(═O)O—, —S(═O)$_2$—, —Si(R$^c$R$^d$)$_2$—, and —C(═O)NR$^e$— (wherein, R$^b$, R$^c$, R$^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), EWG$^1$, EWG$^2$, and EWG$^3$ are an electron withdrawing functional group, R$^1$, R$^2$, and R$^3$ are hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, a1, b1, and c1 are independently an integer of 1 to 3, and a1+a2, b1+b2, and c1+c2 are independently an integer of less than or equal to 5.

[Chemical Formula 1-2]

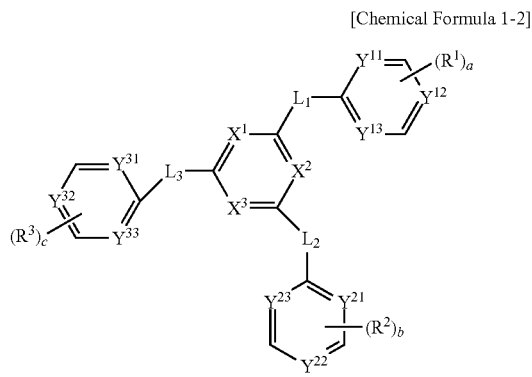

In Chemical Formula 1-2,

X$^1$, X$^2$, and X$^3$ are CR$^a$ or N (wherein R$^a$ is hydrogen, deuterium, a halogen, a C1 to C10 alkyl group, a C1 to C10 haloalkyl group, a C6 to C10 aryl group, or a C2 to C10 heteroaryl group), L$^1$, L$^2$, and L$^3$ are independently a single bond, a substituted or unsubstituted C1 to C30 alkylene group, a substituted or unsubstituted C2 to C30 alkenylene group, a substituted or unsubstituted C2 to C30 alkynylene group, or a substituted or unsubstituted C1 to C30 alkylene group, a substituted or unsubstituted C2 to C30 alkenylene group, or a substituted or unsubstituted C2 to C30 alkynylene group that includes at least one linker selected from —NR$^b$—, —C(═O)—, —S(═O)—, —OC(═O)—, —C(═O)O—, —S(═O)$_2$—, —Si(R$^c$R$^d$)$_2$—, and —C(═O)NR$^e$— (wherein, R$^b$, R$^c$, R$^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), Y$^{11}$, Y$^{12}$, and Y$^{13}$ are independently CR$^f$ or N (wherein R$^f$ is hydrogen, deuterium, a halogen, a C1 to C10 alkyl group, a C1 to C10 haloalkyl group, a C6 to C10 aryl group, or a C2 to C10 heteroaryl group), R$^1$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, a is an integer of 0 to 2, Y$^{21}$, Y$^{22}$, and Y$^{23}$ are independently CR$^g$ or N (wherein R$^g$ is hydrogen, deuterium, a halogen, a C1 to C10 alkyl group, a C1 to C10 haloalkyl group, a C6 to C10 aryl group, or a C2 to C10 heteroaryl group), R$^2$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, b is an integer of 0 to 2, Y$^{31}$, Y$^{32}$, and Y$^{33}$ are independently CR$^h$ or N (wherein R$^h$ is hydrogen, deuterium, a halogen, a C1 to C10 alkyl group, a C1 to C10 haloalkyl group, a C6 to C10 aryl group, or a C2 to C10 heteroaryl group), R$^3$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, c is an integer of 0 to 2, and at least one of Y$^{11}$, Y$^{12}$, and Y$^{13}$, Y$^{21}$, Y$^{22}$, and Y$^{23}$, Y$^{31}$, Y$^{32}$, and Y$^{33}$ is N.

In some embodiments, in Chemical Formulas 1-1 and 1-2, L$^1$, L$^2$, and L$^3$ may independently be a C1 to C30 alkylene group substituted with an electron withdrawing functional group, a C2 to C30 alkenylene group substituted with an electron withdrawing functional group, or a C2 to C30 alkynylene group substituted with an electron withdrawing functional group.

In some embodiments, the electron withdrawing functional group may be a halogen, a C1 to C10 haloalkyl group, a cyano group (—CN), a cyano-containing group, a nitro group (—NO$_2$), a C1 to C10 carboxyl group, a carbonyl group (—C(═O)R, wherein R is a C1 to C10 alkyl group, a C2 to C10 heteroalkyl group, a C6 to C14 aryl group, or a C2 to C10 heteroaryl group), or a C2 to C30 N-containing heteroaryl group.

According to example embodiments, an n-type semiconductor including a compound represented by Chemical Formula 2 is provided.

[Chemical Formula 2]

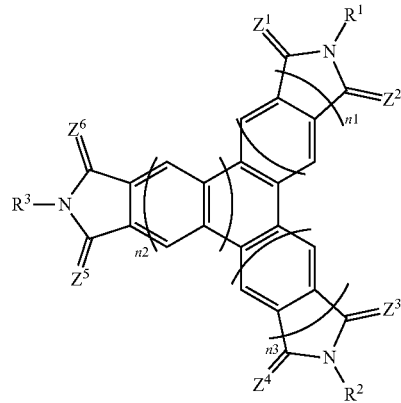

In Chemical Formula 2,

Z$^1$ to Z$^6$ are independently O, S, Se, Te, or C(R)(CN) (wherein R is hydrogen, deuterium, a cyano group (—CN), or a C1 to C10 alkyl group), R$^1$, R$^2$, and R$^3$ are independently hydrogen, deuterium, a halogen, a C1 to C10 alkyl group, a C1 to C10 haloalkyl group, a C2 to C10 heteroalkyl group, a C6 to C14 aryl group, or a C2 to C10 heteroaryl group, and n1, n2, and n3 are independently 0 or 1.

According to example embodiments, a thin film including the n-type semiconductor is provided.

Example embodiments provide an organic photoelectric device including a first electrode and a second electrode facing each other and an active layer between the first electrode and the second electrode, wherein the active layer includes the aforementioned n-type semiconductor.

In some embodiments, the active layer may further include fullerene or a fullerene derivative as an n-type semiconductor.

According to example embodiments, an image sensor including the organic photoelectric device is provided.

According to example embodiments, an electronic device including the organic photoelectric device is provided.

The n-type semiconductor may improve color clarity of the organic photoelectric device by reducing absorption of a blue region.

DETAILED DESCRIPTION

Figure 1:
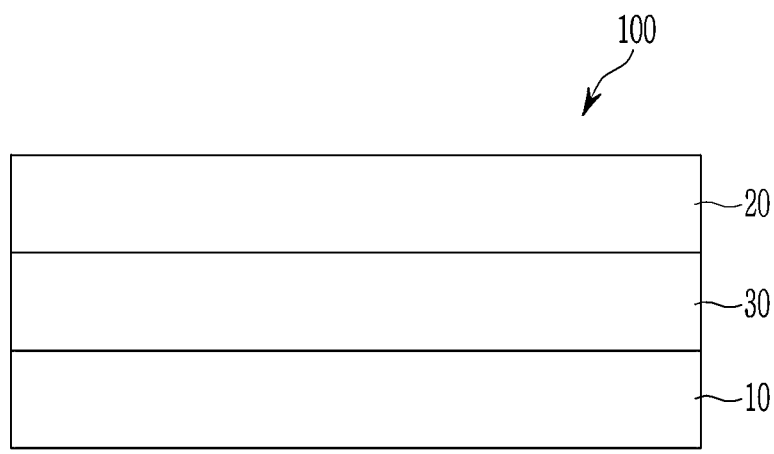
FIG. 1 is a cross-sectional view illustrating an organic photoelectric device according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "combination" includes two or more mixtures, intersubstitutions, and two or more stacked structures.

As used herein, when specific definition is not otherwise provided, "substituted" refers to replacement of a hydrogen of a compound, a functional group, or a moiety by a halogen atom (—F, —Cl, —Br, or —I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C1 to C20 alkoxy group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, or a combination thereof (e.g., a C1 to C20 haloalkyl group such as a C1 to C20 trifluoroalkyl group).

As used herein, when a definition is not otherwise provided, "hetero" refers to one including one to three heteroatoms selected from N, O, S, P, and Si, and remaining carbons in a compound, a functional group, or a moiety.

As used herein, when a definition is not otherwise provided, "aryl group" refers to a group including at least one hydrocarbon aromatic moiety, for example all the elements of the hydrocarbon aromatic moiety having p-orbitals which form conjugation such as a phenyl group or a naphthyl group; two or more hydrocarbon aromatic moieties linked by a sigma bond such as a biphenyl group, a terphenyl group, or a quarterphenyl group; and two or more hydrocarbon aromatic moieties fused directly or indirectly to provide a non-aromatic fused ring such as a fluorenyl group.

As used herein, when a definition is not otherwise provided, "alkyl group" refers to a linear or branched alkyl group and specific examples thereof may include methyl, ethyl, propyl, isopropyl, isobutyl, sec-butyl, pentyl, isoamyl, hexyl, and the like.

As used herein, when a definition is not otherwise provided, "heteroalkyl group" refers to an alkyl group including 1 to 3 heteroatoms selected from N, O, S, P, and Si in the chain.

As used herein, when a definition is not otherwise provided, "halogen" refers to —F, —Cl, —Br, or —I and "haloalkyl group" refers to an alkyl group in which at least one hydrogen is replaced by a halogen.

As used herein, when a definition is not otherwise provided, "heteroalkyl group" refers to an alkyl group including 1 to 3 heteroatoms selected from N, O, S, P, and Si.

As used herein, when a definition is not otherwise provided, "heteroaryl group" refers to an aryl group including at least one heteroatom, wherein the heteroatom may be for example N, O, S, P, and/or Si, but is not limited thereto. At least two heteroaryl groups may be linked directly through a sigma bond or at least two heterocyclic groups may be fused with each other. When the heteroaryl group is a fused ring, each ring may include one to three heteroatoms.

As used herein, when specific definition is not otherwise provided, "cyano-containing group" refers to a C1 to C30 alkyl group, a C2 to C30 alkenyl group, or a C2 to C30 alkynyl group in which at least one hydrogen is replaced by a cyano group. In addition, the cyano-containing group may include a divalent functional group such as a functional group represented by $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group. As used herein, the cyano-containing group does not include a functional group containing only the cyano group (—CN).

Hereinafter, an n-type semiconductor according to example embodiments is described.

According to example embodiments, an n-type semiconductor includes a compound represented by Chemical Formula 1.

[Chemical Formula 1]

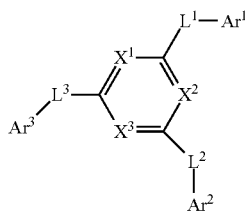

In Chemical Formula 1, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $L^1$, $L^2$, and $L^3$ are independently a single bond; a substituted or unsubstituted C1 to C30 alkylene group; a substituted or unsubstituted C2 to C30 alkenylene group; a substituted or unsubstituted C2 to C30 alkynylene group; or a substituted or unsubstituted C1 to C30 alkylene group, a substituted or unsubstituted C2 to C30 alkenylene group, or a substituted or unsubstituted C2 to C30 alkynylene group that includes at least one linker selected from —$NR^b$—, —C(=O)—, —S(=O)—, —OC(=O)—, —C(=O)O—, —S(=O)$_2$—, —Si($R^c R^d$)$_2$—, and —C(=O)$NR^e$— (wherein, $R^b$, $R^c$, $R^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), and $Ar^1$, $Ar^2$ and $Ar^3$ are independently C2 to C30 N-containing heteroaryl group, a C6 to C30 aryl group having at least one electron withdrawing functional group (EWG) or a C2 to C30 heteroaryl group having at least one electron withdrawing functional group.

In example embodiments, in Chemical Formula 1, at least one of $X^1$, $X^2$, and $X^3$ may be N.

In example embodiments, in Chemical Formula 1, $L^1$, $L^2$, and $L^3$ may independently be a C1 to C30 alkylene group substituted with an electron withdrawing functional group, a C2 to C30 alkenylene group substituted with an electron withdrawing functional group, or a C2 to C30 alkynylene group substituted with an electron withdrawing functional group. Examples of the C2 to C30 alkenylene group substituted with an electron withdrawing functional group may be a fluorovinylene group, a cyanovinylene group, and the like.

The electron withdrawing functional group may be a halogen (e.g., fluoro (—F) group), a C1 to C10 haloalkyl group (e.g., a fluoroalkyl group such as a trifluoromethyl group (—$CF_3$)), a cyano group (—CN), a cyano-containing group, a nitro group (—$NO_2$), a C1 to C10 carboxyl group (e.g., an acetate group), a carbonyl group (—C(=O)R, wherein R is a C1 to C10 alkyl group, a C2 to C10 heteroalkyl group, a C6 to C14 aryl group, or a C2 to C10 heteroaryl group), or a C2 to C30 N-containing heteroaryl group (e.g., a pyrrolyl group, a pyridyl group, a pyridmidyl group, or a triazinyl group).

The compound represented by Chemical Formula 1 may be a compound represented by Chemical Formula 1-1.

[Chemical Formula 1-1]

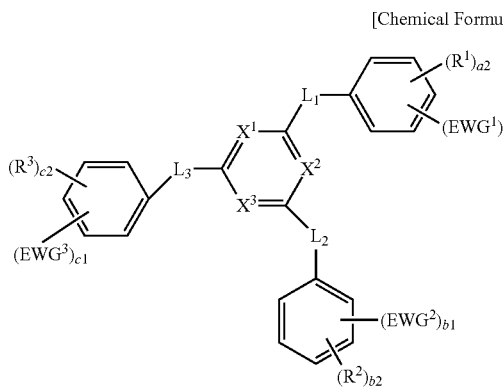

In Chemical Formula 1-1, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $L^1$, $L^2$, and $L^3$ are independently a single bond; a substituted or unsubstituted C1 to C30 alkylene group; a substituted or unsubstituted C2 to C30 alkenylene group; a substituted or unsubstituted C2 to C30 alkynylene group; or a substituted or unsubstituted C1 to C30 alkylene group, a substituted or unsubstituted C2 to C30 alkenylene group, or a substituted or unsubstituted C2 to C30 alkynylene group that includes at least one linker selected from —$NR^b$—, —C(=O)—, —S(=O)—, —OC(=O)—, —C(=O)O—, —S(=O)$_2$—, —Si($R^c R^d$)$_2$—, and —C(=O)$NR^e$— (wherein, $R^b$, $R^c$, $R^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), $EWG^1$, $EWG^2$, and $EWG^3$ are an electron withdrawing functional group, $R^1$, $R^2$, and $R^3$ are hydrogen, deuterium, a C1 to C10 alkyl group, a C2 to C10 heteroalkyl group, a C6 to C14 aryl group, or a C2 to C10 heteroaryl group, a1, b1, and c1 are independently an integer of 1 to 3, and a1+a2, b1+b2, and c1+c2 are independently less than or equal to 5.

In example embodiments, in Chemical Formula 1-1, at least one of $X^1$, $X^2$, and $X^3$ may be N.

In Chemical Formula 1-1, $L^1$, $L^2$, and $L^3$ may independently be a C1 to C30 alkylene group substituted with an electron withdrawing functional group, a C2 to C30 alkenylene group substituted with an electron withdrawing functional group, or a C2 to C30 alkynylene group substituted with an electron withdrawing functional group. Examples of the C2 to C30 alkenylene group substituted with an electron withdrawing functional group may be a fluorovinylene group, a cyanovinylene group, and the like.

The electron withdrawing functional group may be a halogen (e.g., a fluoro (—F) group), a C1 to C10 haloalkyl group (e.g., a fluoroalkyl group such as a trifluoromethyl group (—$CF_3$)), a cyano group (—CN), a cyano-containing group, a nitro group (—$NO_2$), a C1 to C10 carboxyl group (e.g., an acetate group), a carbonyl group (—C(=O)R, wherein R is a C1 to C10 alkyl group, a C2 to C10 heteroalkyl group, a C6 to C14 aryl group, or a C2 to C10 heteroaryl group), or a C2 to C30 N-containing heteroaryl group (e.g., a pyrrolyl group, a pyridyl group, a pyridmidyl group, or a triazinyl group).

The compound represented by Chemical Formula 1-1 may be a compound represented by Chemical Formula 1-1A.

[Chemical Formula 1-1A]

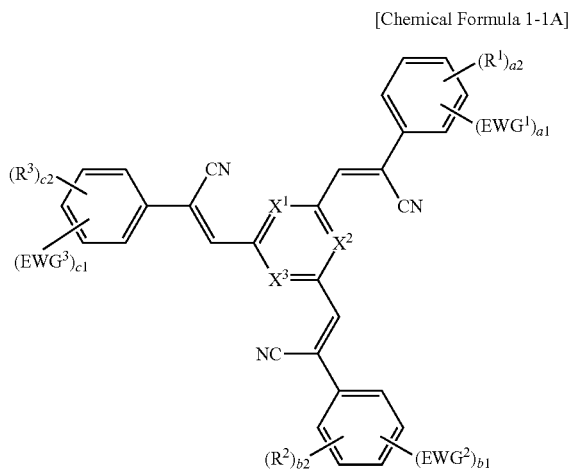

In Chemical Formula 1-1A, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $EWG^1$, $EWG^2$, and $EWG^3$ are an electron withdrawing functional group, $R^1$, $R^2$, and $R^3$ are hydrogen, deuterium, a C1 to C10 alkyl group, a C2 to C10 heteroalkyl group, a C6 to C14 aryl group, or a C2 to C10 heteroaryl group, a1, b1, and c1 are independently an integer of 1 to 3, and a1+a2, b1+b2, and c1+c2 are independently less than or equal to 5.

The compound represented by Chemical Formula 1 may be a compound represented by Chemical Formula 1-2.

[Chemical Formula 1-2]

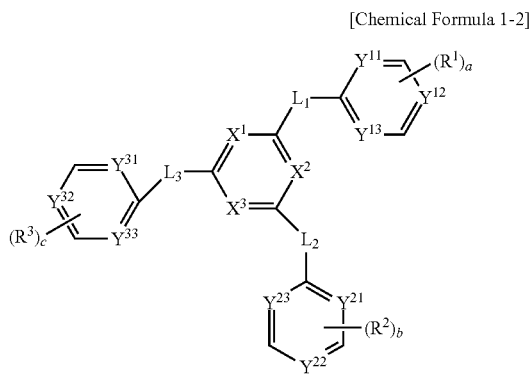

In Chemical Formula 1-2, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $L^1$, $L^2$, and $L^3$ are independently a single bond; a substituted or unsubstituted C1 to C30 alkylene group; a substituted or unsubstituted C2 to C30 alkenylene group; a substituted or unsubstituted C2 to C30 alkynylene group; or a substituted or unsubstituted C1 to C30 alkylene group, a substituted or unsubstituted C2 to C30 alkenylene group, or a substituted or unsubstituted C2 to C30 alkynylene group that includes at least one linker selected from $-NR^b-$, $-C(=O)-$, $-S(=O)-$, $-OC(=O)-$, $-C(=O)O-$, $-S(=O)_2-$, $-Si(R^cR^d)_2-$, and $-C(=O)NR^e-$ (wherein, $R^b$, $R^c$, $R^d$, and Re are independently hydrogen, deuterium, a C1 to C10 alkyl group, a C2 to C10 alkenyl group, a C2 to C10 alkynyl group, a C6 to C18 aryl group, or a C2 to C18 heteroaryl group), $Y^{11}$, $Y^{12}$, and $Y^{13}$ are independently $CR^f$ or N (wherein $R^f$ is hydrogen, deuterium, a halogen, a C1 to C10 alkyl group, a C1 to C10 haloalkyl group, a C6 to C10 aryl group, or a C2 to C10 heteroaryl group), $R^1$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, a is an integer of 0 to 2, $Y^{21}$, $Y^{22}$, and $Y^{23}$ are independently $CR^g$ or N (wherein $R^g$ is hydrogen, deuterium, a halogen, a C1 to C10 alkyl group, a C1 to C10 haloalkyl group, a C6 to C10 aryl group, or a C2 to C10 heteroaryl group), $R^2$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, b is an integer of 0 to 2, $Y^{31}$, $Y^{32}$, and $Y^{33}$ are independently $CR^h$ or N (wherein $R^h$ is hydrogen, deuterium, a halogen, a C1 to C10 alkyl group, a C1 to C10 haloalkyl group, a C6 to C10 aryl group, or a C2 to C10 heteroaryl group), $R^3$ is hydrogen, deuterium, a halogen, a cyano group, a C1 to C10 alkyl group, a C1 to C10 haloalkyl group, a C2 to C10 heteroalkyl group, a C6 to C14 aryl group, or a C2 to C10 heteroaryl group, c is an integer of 0 to 2, and at least one of $Y^{11}$, $Y^{12}$, and $Y^{13}$, $Y^{21}$, $Y^{22}$, and $Y^{23}$, $Y^{31}$, $Y^{32}$, and $Y^{33}$ is at N.

In Chemical Formula 1-2, at least two of $Y^{11}$, $Y^{12}$, and $Y^{13}$, $Y^{21}$, $Y^{22}$, and $Y^{23}$, $Y^{31}$, $Y^{32}$, and $Y^{33}$ may be N.

In example embodiments, in Chemical Formula 1-2, at least one of $Y^{11}$, $Y^{12}$, and $Y^{13}$ may be N, at least one of $Y^{21}$, $Y^{22}$, and $Y^{23}$ may be N, and at least one of $Y^{31}$, $Y^{32}$, and $Y^{33}$ may be N.

In example embodiments, in Chemical Formula 1-2, at least one of $X^1$, $X^2$, and $X^3$ may be N.

In Chemical Formula 1-2, $L^1$, $L^2$, and $L^3$ may independently be a C1 to C30 alkylene group substituted with an electron withdrawing functional group, a C2 to C30 alkenylene group substituted with an electron withdrawing functional group, or a C2 to C30 alkynylene group substituted with an electron withdrawing functional group. Examples of the C2 to C30 alkenylene group substituted with an electron withdrawing functional group may be a fluorovinylene group, a cyanovinylene group, and the like.

The electron withdrawing functional group may be a halogen (e.g., fluoro (—F) group), a C1 to C10 haloalkyl group (e.g., a fluoroalkyl group such as a trifluoromethyl group ($-CF_3$)), a cyano group (—CN), a cyano-containing group, a nitro group ($-NO_2$), a C1 to C10 carboxyl group (e.g., an acetate group), a carbonyl group (—C(=O)R, wherein R is a C1 to C10 alkyl group, a C2 to C10 heteroalkyl group, a C6 to C14 aryl group, or a C2 to C10 heteroaryl group), or a C2 to C30 N-containing heteroaryl group (e.g., a pyrrolyl group, a pyridyl group, a pyridmidyl group, or a triazinyl group).

The compound represented by Chemical Formula 1-2 may be a compound represented by Chemical Formula 1-2A.

[Chemical Formula 1-2A]

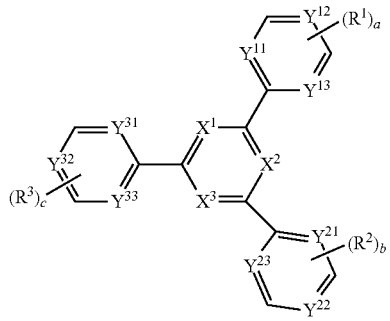

[Chemical Formula 1-2B]

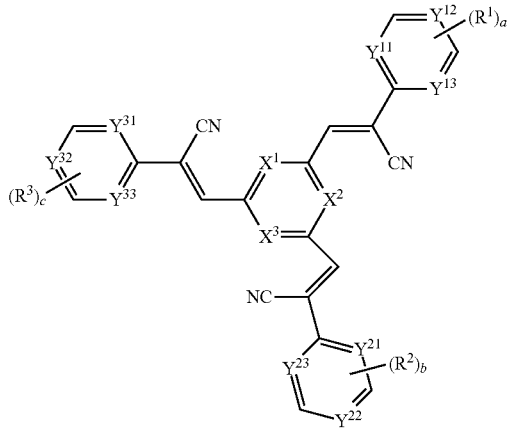

In Chemical Formula 1-2A, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $Y^{11}$, $Y^{12}$ and $Y^{13}$ are independently $CR^f$ or N (wherein $R^f$ is hydrogen, deuterium, a halogen, a C1 to C10 alkyl group, a C1 to C10 haloalkyl group, a C6 to C10 aryl group, or a C2 to C10 heteroaryl group), $R^1$ is hydrogen, deuterium, a halogen, a C1 to C10 alkyl group, a C1 to C10 haloalkyl group, a C2 to C10 heteroalkyl group, a C6 to C14 aryl group, or a C2 to C10 heteroaryl group, a is an integer of 0 to 2, $Y^{21}$, $Y^{22}$, and $Y^{23}$ are independently $CR^g$ or N (wherein $R^g$ is hydrogen, deuterium, a halogen, a C1 to C10 alkyl group, a C1 to C10 haloalkyl group, a C6 to C10 aryl group, or a C2 to C10 heteroaryl group), $R^2$ is hydrogen, deuterium, a halogen, a C1 to C10 alkyl group, a C1 to C10 haloalkyl group, a C6 to C10 aryl group, or a C2 to C10 heteroaryl group, b is an integer of 0 to 2, $Y^{31}$, $Y^{32}$, and $Y^{33}$ are independently $CR^h$ or N (wherein $R^h$ is hydrogen, deuterium, a halogen, a C1 to C10 alkyl group, a C1 to C10 haloalkyl group, a C6 to C10 aryl group, or a C2 to C10 heteroaryl group), $R^3$ is hydrogen, deuterium, a halogen, a C1 to C10 alkyl group, a C1 to C10 haloalkyl group, a C6 to C10 aryl group, or a C2 to C10 heteroaryl group, c is an integer of 0 to 2, and at least one of $Y^{11}$, $Y^{12}$, and $Y^{13}$, $Y^{21}$, $Y^{22}$, and $Y^{23}$, $Y^{31}$, $Y^{32}$, and $Y^{33}$ is at N.

In Chemical Formula 1-2A, at least two of $Y^{11}$, $Y^{12}$, and $Y^{13}$, $Y^{21}$, $Y^{22}$, and $Y^{23}$, $Y^{31}$, $Y^{32}$, and $Y^{33}$ may be N.

In example embodiments, in Chemical Formula 1-2A, at least one of $Y^{11}$, $Y^{12}$, and $Y^{13}$ may be N, at least one of $Y^{21}$, $Y^{22}$, and $Y^{23}$ may be N, and at least one of $Y^{31}$, $Y^{32}$, and $Y^{33}$ may be N.

The compound represented by Chemical Formula 1 may be a compound represented by Chemical Formula 1-2B.

In Chemical Formula 1-2B, $X^1$, $X^2$, and $X^3$ are $CR^a$ or N (wherein $R^a$ is hydrogen, deuterium, a halogen, a C1 to C10 alkyl group, a C1 to C10 haloalkyl group, a C6 to C10 aryl group, or a C2 to C10 heteroaryl group), $Y^{11}$, $Y^{12}$, and $Y^{13}$ are independently $CR^f$ or N (wherein $R^f$ is hydrogen, deuterium, a halogen, a C1 to C10 alkyl group, a C1 to C10 haloalkyl group, a C6 to C10 aryl group, or a C2 to C10 heteroaryl group), $R^1$ is hydrogen, deuterium, a halogen, a C1 to C10 alkyl group, a C1 to C10 haloalkyl group, a C6 to C10 aryl group, or a C2 to C10 heteroaryl group, a is an integer of 0 to 2, $Y^{21}$, $Y^{22}$, and $Y^{23}$ are independently $CR^g$ or N (wherein $R^g$ is hydrogen, deuterium, a halogen, a C1 to C10 alkyl group, a C1 to C10 haloalkyl group, a C6 to C10 aryl group, or a C2 to C10 heteroaryl group), $R^2$ is hydrogen, deuterium, a halogen, a C1 to C10 alkyl group, a C1 to C10 haloalkyl group, a C6 to C10 aryl group, or a C2 to C10 heteroaryl group, b is an integer of 0 to 2, $Y^{31}$, $Y^{32}$, and $Y^{33}$ are independently $CR^h$ or N (wherein $R^h$ is hydrogen, deuterium, a halogen, a C1 to C10 alkyl group, a C1 to C10 haloalkyl group, a C6 to C10 aryl group, or a C2 to C10 heteroaryl group), $R^3$ is hydrogen, deuterium, a halogen, a C1 to C10 alkyl group, a C1 to C10 haloalkyl group, a C6 to C10 aryl group, or a C2 to C10 heteroaryl group, c is an integer of 0 to 2, and at least one of $Y^{11}$, $Y^{12}$, and $Y^{13}$, $Y^{21}$, $Y^{22}$, and $Y^{23}$, $Y^{31}$, $Y^{32}$, and $Y^{33}$ is at N.

In Chemical Formula 1-2B, at least two of $Y^{11}$, $Y^{12}$, and $Y^{13}$, $Y^{21}$, $Y^{22}$, and $Y^{23}$, $Y^{31}$, $Y^{32}$, and $Y^{33}$ may be N. In example embodiments, in Chemical Formula 1-2B, at least one of $Y^{11}$, $Y^{12}$, and $Y^{13}$ may be N, at least one of $Y^{21}$, $Y^{22}$, and $Y^{23}$ may be N, and at least one of $Y^{31}$, $Y^{32}$, and $Y^{33}$ may be N.

According to example embodiments, an n-type semiconductor includes a compound represented by Chemical Formula 2.

[Chemical Formula 2]

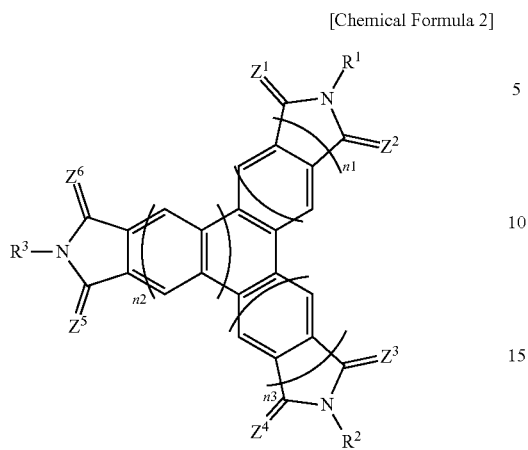

In Chemical Formula 2, $Z^1$ to $Z^6$ are independently O, S, Se, Te, or C(R)(CN) (wherein R is hydrogen, deuterium, a cyano group (—CN), or a C1 to C10 alkyl group), $R^1$, $R^2$, and $R^3$ are independently hydrogen, deuterium, a halogen, a C1 to C10 alkyl group, a C1 to C10 haloalkyl group, a C2 to C10 heteroalkyl group, a C6 to C14 aryl group, or a C2 to C10 heteroaryl group, and n1, n2, and n3 are independently 0 or 1.

In the compound represented by Chemical Formula 1, Chemical Formula 1-1 (including Chemical Formula 1-1A), Chemical Formula 1-2 (including Chemical Formula 1-2A, Chemical Formula 1-2B) or Chemical Formula 2, substituents are present symmetrically in the center of the benzene ring or heteroatomo-containing aromatic ring which is present in the core to limit and/or prevent agglomeration from each other by maintaining a constant distance between the compounds.

Specific examples of the compound represented by Chemical Formula 1-1 may include compounds of Group 1.

[Group 1]

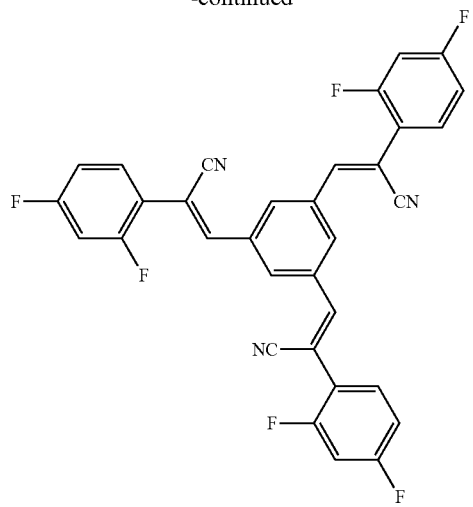

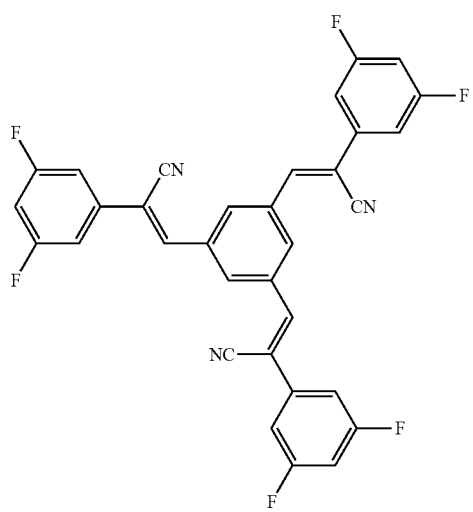

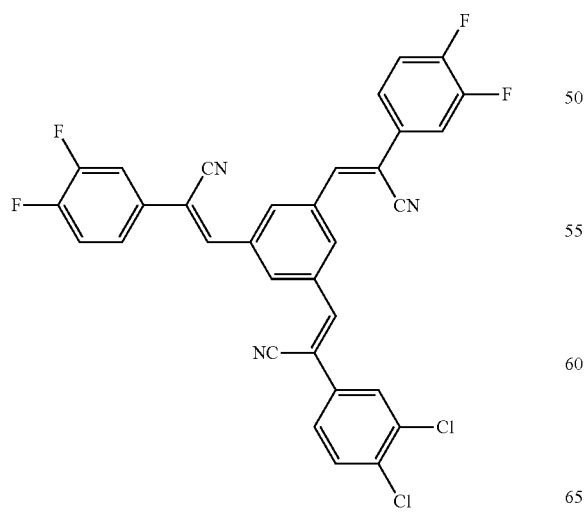

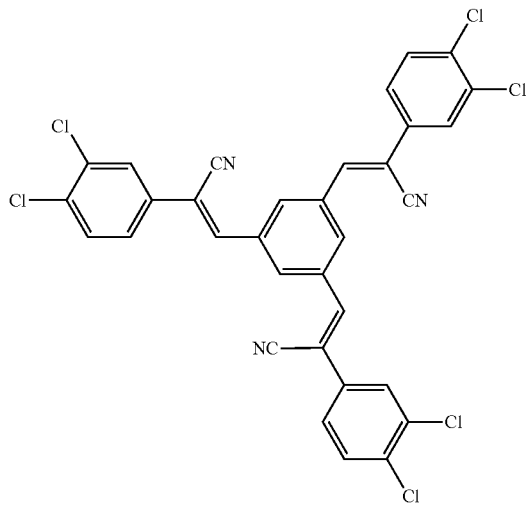

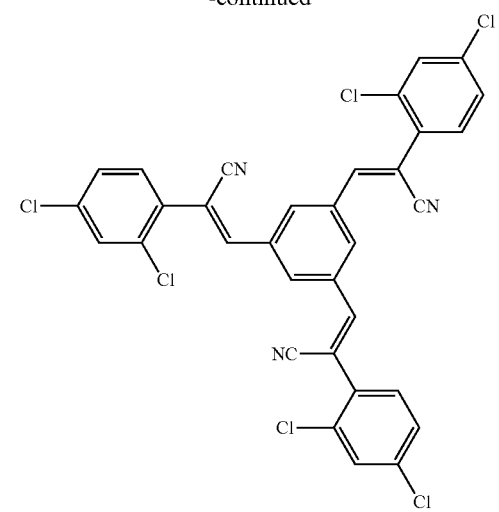

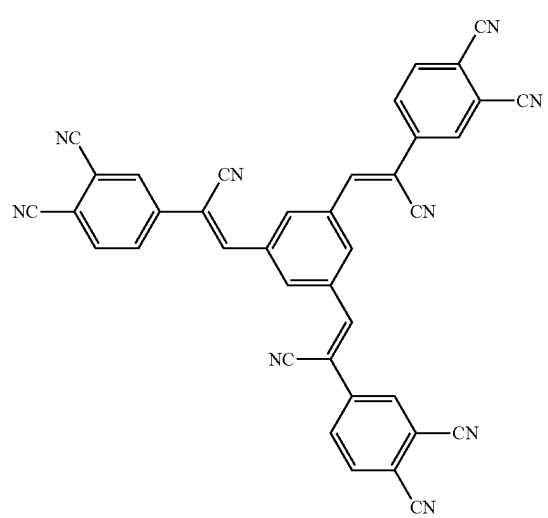

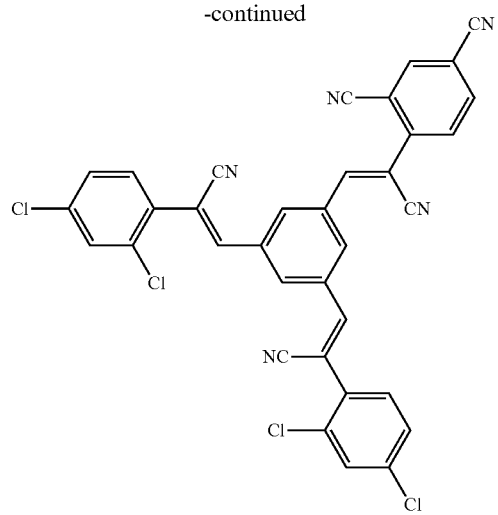

In Group 1, the hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof.

Specific examples of the compound represented by Chemical Formula 1-2 include compounds of Group 2.
[Group 2]
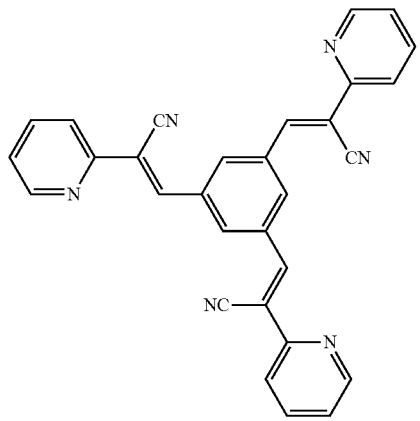
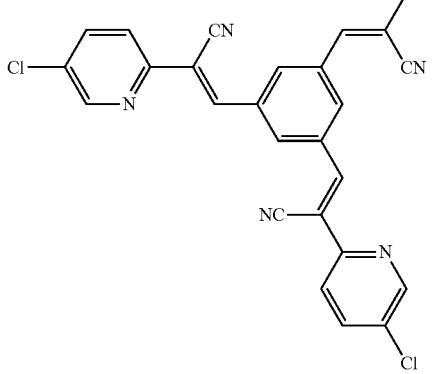
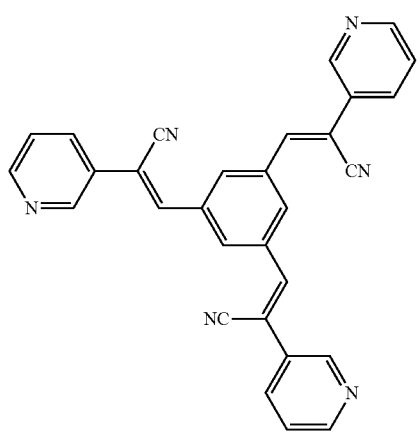
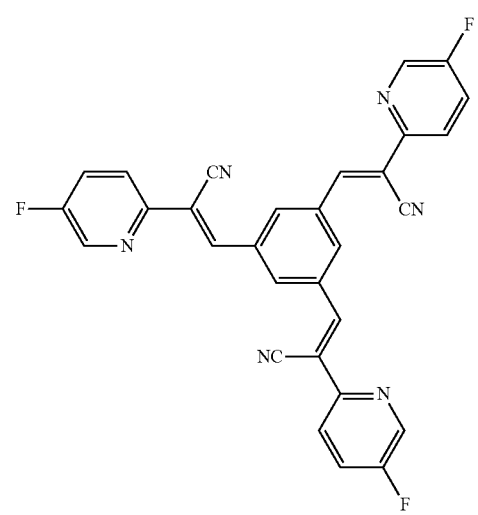
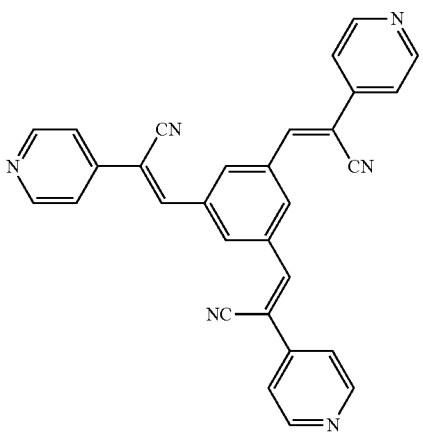
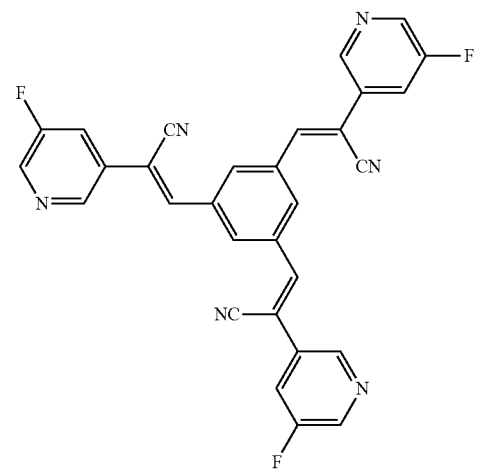

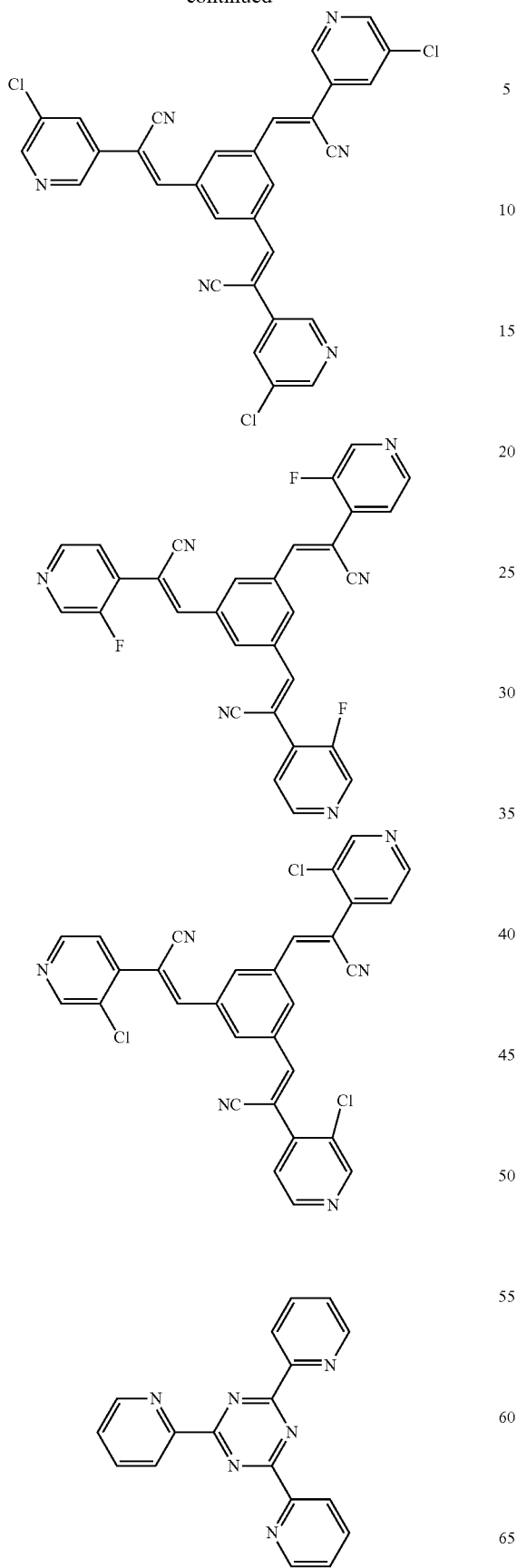
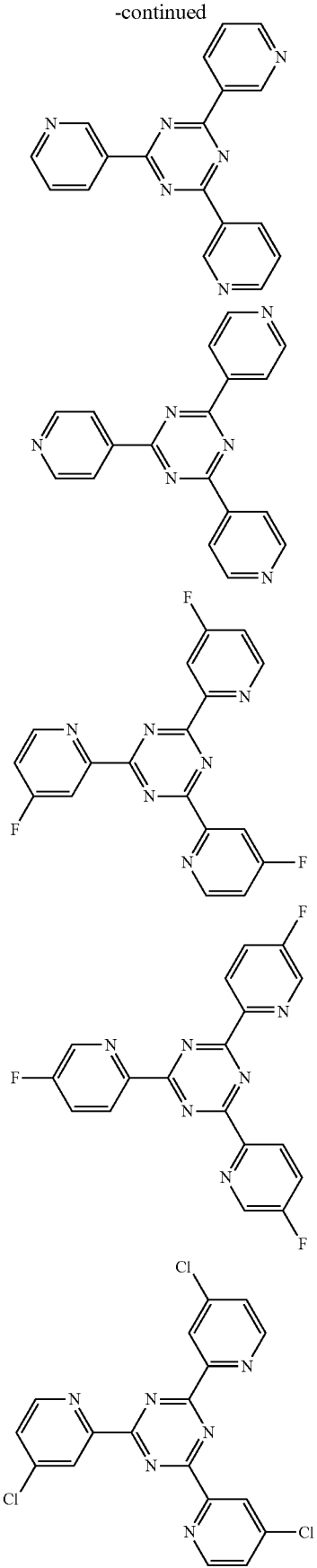

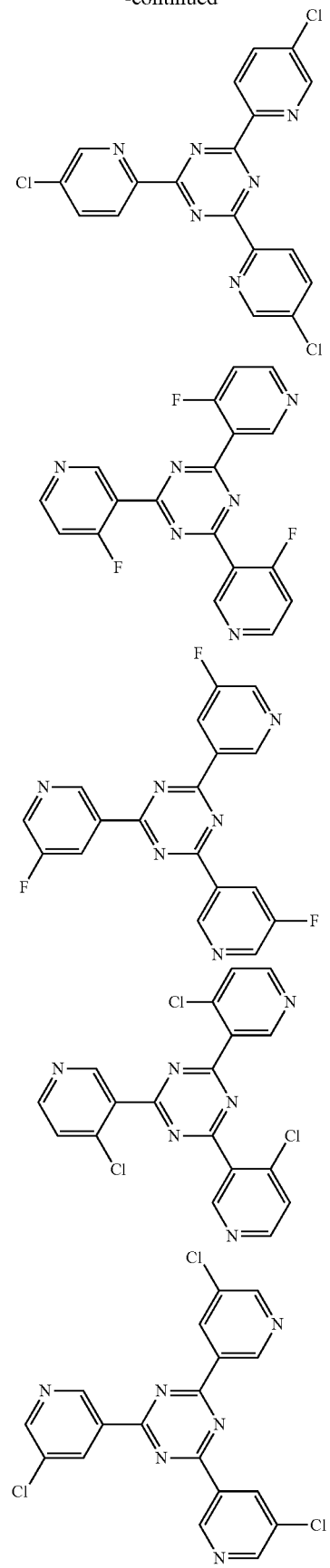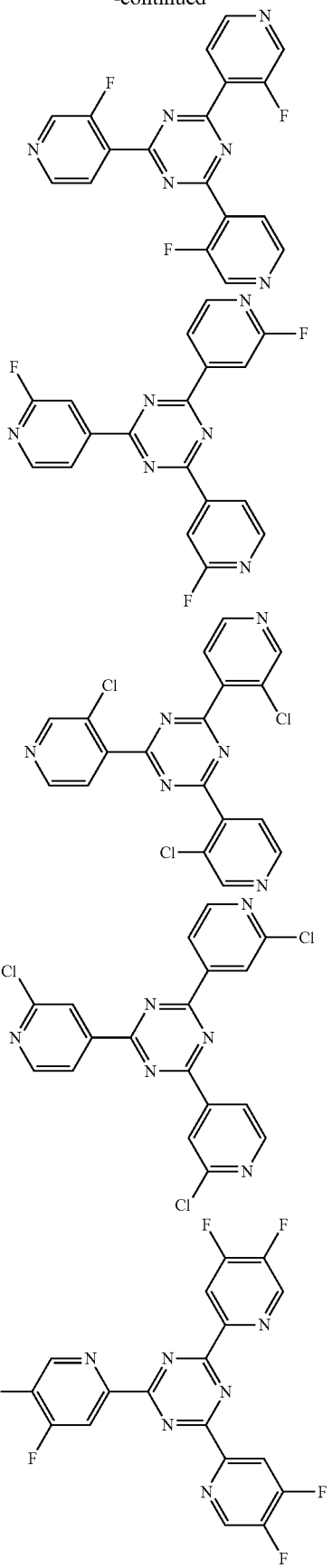

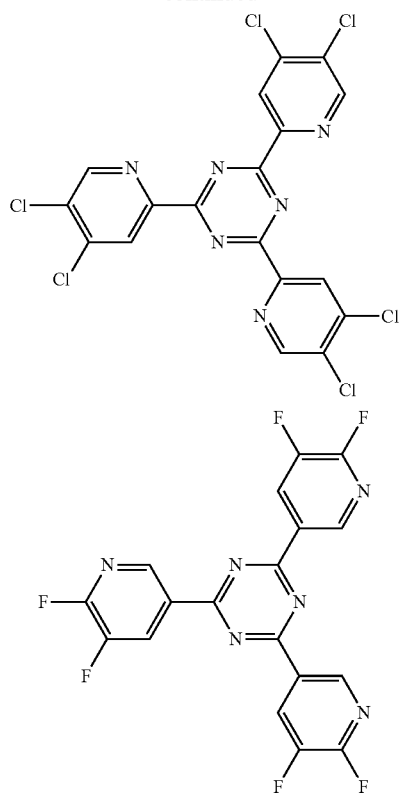
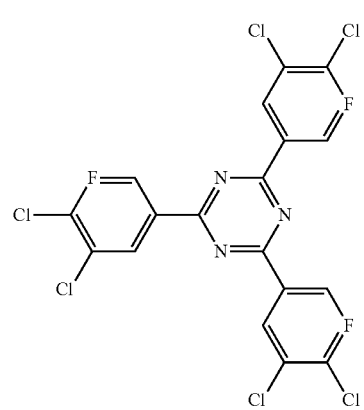
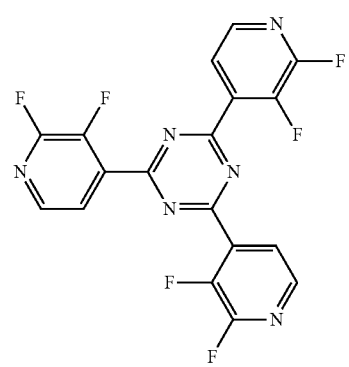
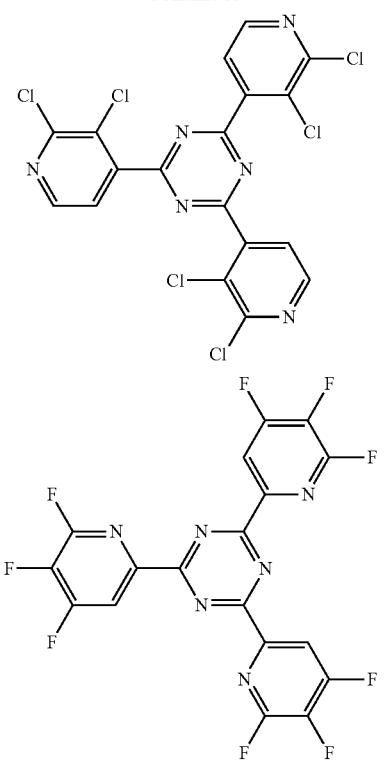
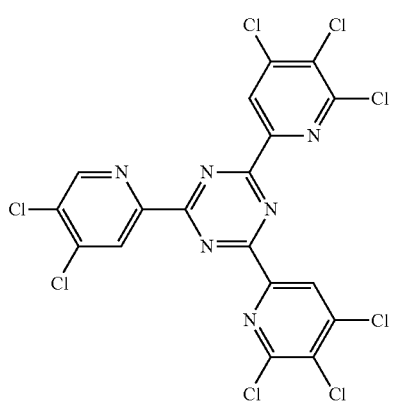
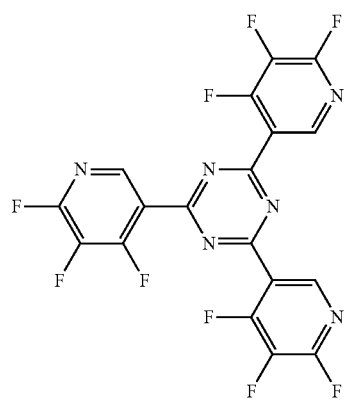

-continued

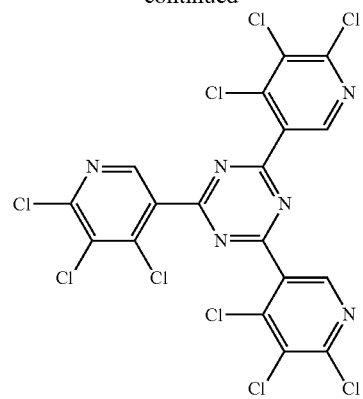

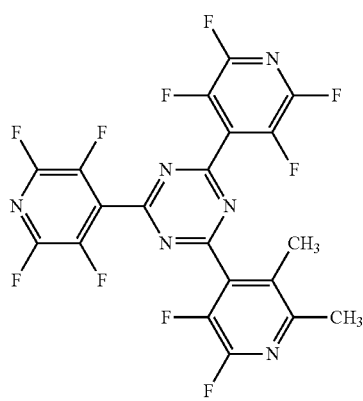

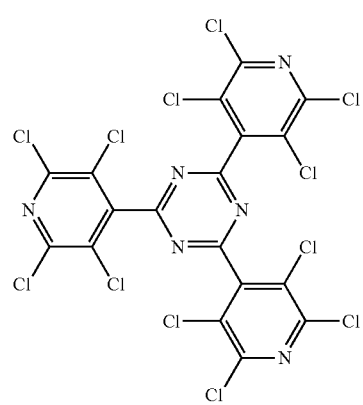

In Group 2, the hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof.

Specific examples of the compound represented by Chemical Formula 2 include compounds of Group 3.

[Group 3]

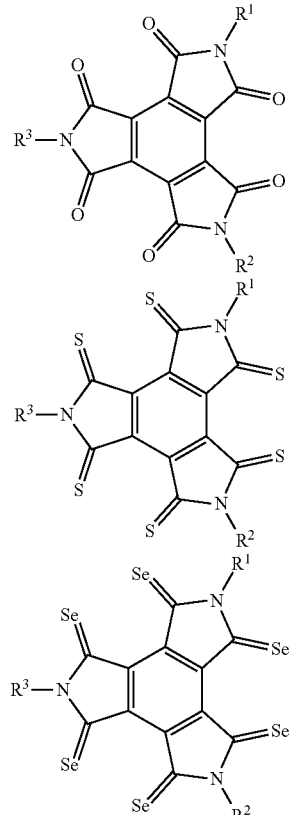

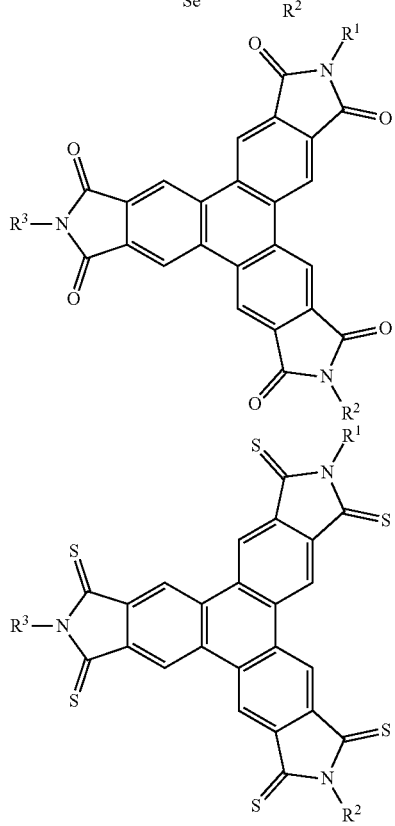

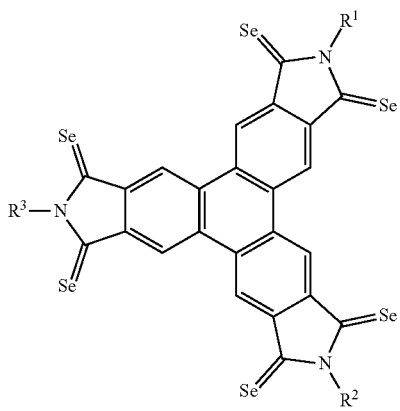

In Group 3,

R[1], R[2], and R[3] may independently be hydrogen, deuterium, a C1 to C10 alkyl group, a C1 to C10 haloalkyl group, a C2 to C10 heteroalkyl group, a C6 to C14 aryl group, or a C2 to C10 heteroaryl group, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof.

Specific examples of Group 3 include compounds of Group 3-1.

[Group 3-1]

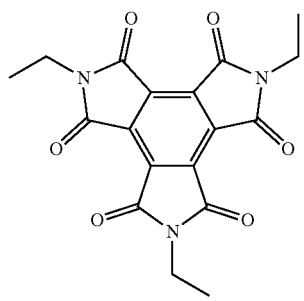

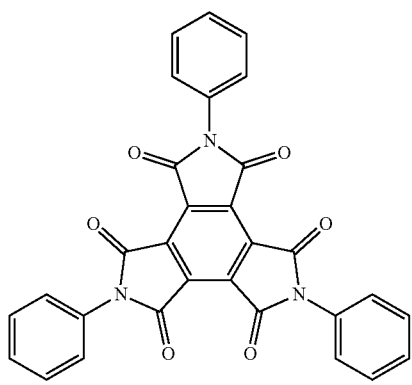

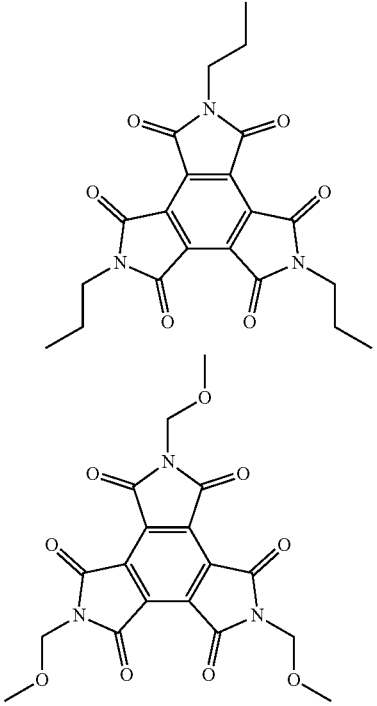

In Group 3-1, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof.

According to example embodiments, a thin film including the n-type semiconductor is provided. The absorption of the blue region of C60 (about 450 nm region) is known to be due to aggregation of C60 (Journal of Molecular Structure 526 (2000) 25-29). An absorption coefficient at a wavelength of about 450 nm of the thin film including the n-type semiconductor may be smaller than an absorption coefficient at a wavelength of about 450 nm of the thin film including unsubstituted C60 fullerene. This is because agglomeration of the n-type semiconductor is suppressed by the n-type semiconductor including electron withdrawing substituents having a symmetrical structure.

The n-type semiconductor may be formed into a thin film using vacuum deposition by sublimation.

In example embodiments, the thin film may include a compound represented by Chemical Formula 1, a compound represented by Chemical Formula 2, or a combination thereof. When the thin film includes the compound represented by Chemical Formula 1 and the compound represented by Chemical Formula 2, the compound represented by Chemical Formula 1 and the compound represented by Chemical Formula 2 may be used in a volume ratio of about 1:9 to about 9:1, about 2:8 to about 8:2, about 3:7 to about 7:3, or about 4:6 to about 6:4. Within the above range, light absorption and electrical properties of the thin film may be easily adjusted.

The thin film may include a first n-type semiconductor including the compound represented by Chemical Formula 1 or Chemical Formula 2 and a second n-type semiconductor including fullerene or a fullerene derivative.

The fullerene may be C60 to C120 fullerene, specifically, C60, C70, C74, C76, C78, C80, C82, C84, C90 or C96, but is not limited thereto.

The fullerene derivative refers to a compound having a substituent on fullerene. Examples of the substituent may be an alkyl group, an aryl group, or a heterocyclic group. The alkyl group may be a C1 to C12 alkyl group, for example a C1 to C5 alkyl group. The aryl group may be a phenyl group, a naphthyl group, or an anthracenyl group. Here, the heterocyclic group may be a furyl group, a thienyl group, a pyrrolyl group, an oxazolyl group, a pyridyl group, a quinolyl group, or a carbazolyl group.

Specific examples of the fullerene derivative may be phenyl-C61-butyric acid methylester (PCBM), PCBM ([6, 6]-phenyl-C61-butyric acid methyl ester), ICBA (indene-C60 bisadduct), and ICMA (indene-C60 monoadduct), but is not limited thereto.

When the thin film includes the first n-type semiconductor and the second n-type semiconductor, the first n-type semiconductor may be used in an amount of less than about 50 volume %, for example, less than or equal to about 45 volume %, less than or equal to about 40 volume %, less than or equal to about 35 volume %, less than or equal to about 30 volume %, or less than or equal to about 25 volume % based on a total amount (100 volume %) of the first n-type semiconductor and the second n-type semiconductor. Within the ranges, unnecessary absorption in the blue region (about 400 nm to about 500 nm) may be decreased, and absorption in the green region may be increased. For example, an absorption coefficient at a wavelength of 450 nm of the thin film including the first n-type semiconductor and the second n-type semiconductor may be smaller than that of a thin film including unsubstituted fullerene (e.g., C60 fullerene), for example, the absorption coefficient at the wavelength of 450 nm of the thin film including the first n-type semiconductor and the second n-type semiconductor may be less than or equal to about 75%, for example, less than or equal to about 50% of that of the thin film including unsubstituted fullerene (e.g., C60 fullerene).

Hereinafter, an organic photoelectric device including the aforementioned n-type semiconductor is described.

FIG. 1 is a cross-sectional view illustrating an organic photoelectric device according to an embodiment.

Referring to FIG. 1, an organic photoelectric device 100 according to an embodiment includes a first electrode 10 and a second electrode 20 facing each other and an active layer 30 disposed between the first electrode 10 and the second electrode 20.

A substrate (not shown) may be disposed at the side of the first electrode 10 or the second electrode 20. The substrate may be for example made of an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 and the second electrode 20 is an anode and the other is a cathode. For example, the first electrode 10 may be a cathode and the second electrode 20 may be an anode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AlTO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The active layer 30 is a layer including a P-type semiconductor and an N-type semiconductor to provide a pn junction, which is a layer producing excitons by receiving light from outside and then separating holes and electrons from the produced excitons.

Each of the p-type semiconductor and the n-type semiconductor may be a light absorbing material that absorbs at least a portion of the light in the visible region. For example, the p-type semiconductor may be a light absorbing material capable of selectively absorbing any one of a wavelength region of greater than or equal to about 400 nm to less than about 500 nm, a wavelength region of about 500 nm to about 600 nm, and/or a wavelength region of greater than about 600 nm and less than or equal to about 700 nm and the n-type semiconductor may be the aforementioned compound represented by Chemical Formula 1 or Chemical Formula 2.

In one example, the p-type semiconductor may be a light absorbing material that selectively absorbs any one of light in a wavelength region of greater than or equal to about 400 nm to less than about 500 nm, a wavelength region of about 500 nm to about 600 nm, and a wavelength region of greater than about 600 nm and less than or equal to about 700 nm. The n-type semiconductor may be the aforementioned compound represented by Chemical Formula 1 or Chemical Formula 2. For example, the p-type semiconductor may be an absorbing material that selectively absorbs light in a wavelength region of about 500 nm to about 600 nm and the n-type semiconductor may be the aforementioned compound represented by Chemical Formula 1 or Chemical Formula 2.

For example, the p-type semiconductor may be, for example, a light absorbing material having a LUMO energy level of about 3.0 eV to about 3.6 eV and a HOMO energy level of about 5.1 eV to about 5.7 eV. Within this range, the p-type semiconductor may be, for example, a light absorbing material having a LUMO energy level of about 3.1 eV to about 3.5 eV and a HOMO energy level of 5.2 eV to about 5.6 eV.

For example, the p-type semiconductor may be a light absorbing material having a core structure including, for example, an electron donating moiety, a pi conjugated linking group, and an electron accepting moiety.

The p-type semiconductor may include, for example, a compound represented by Chemical Formula 3 as the compound having the core structure, but is not limited thereto.

[Chemical Formula 3]

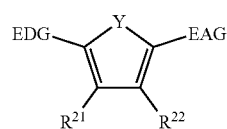

In Chemical Formula 3,
Y is Se, Te, S, SO, $SO_2$, or $SiR^h R^i$,
EDG is an electron donating group,
EAG is an electron accepting group, and $R^{21}$, $R^{22}$, $R^h$, and $R^i$ are independently hydrogen or a monovalent substituent.

Herein, the monovalent substituent may be, for example, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, but is not limited thereto.

The p-type semiconductor may be, for example, a light absorbing material represented by Chemical Formula 3A, but is not limited thereto.

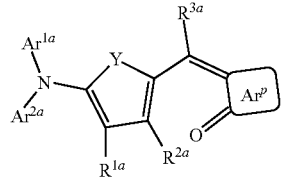

[Chemical Formula 3A]

In Chemical Formula 3A,

Y is Se, Te, S, SO, SO$_2$, or SiR$^h$R$^i$,

Ar$^p$ is a substituted or unsubstituted 5-membered ring, a substituted or unsubstituted 6-membered ring, or a condensed ring of two or more of the foregoing rings, Ar$^{1a}$ and Ar$^{2a}$ are independently a substituted or unsubstituted C6 to C30 aryl group or a substituted or unsubstituted C3 to C30 heteroaryl group, wherein Ar$^{1a}$ and Ar$^{2a}$ are independently present or linked to each other by a linker of G$^1$ to form a ring, wherein G$^1$ is one of a single bond, —(CR$^j$R$^k$)$_{n2}$—, —O—, —S—, —Se—, —N=, —NR$^l$—, —SiR$^m$R$^n$—, —GeR$^o$R$^p$— and n2 is 1 or 2, and R$^{1a}$ to R$^{3a}$ and R$^h$ to R$^p$ are independently hydrogen, deuterium, a substituted or unsubstituted C1 to C30 an alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

The p-type semiconductor may be for example a light absorbing material represented by one of Chemical Formulas 3A-1 to 3A-4, but is not limited thereto.

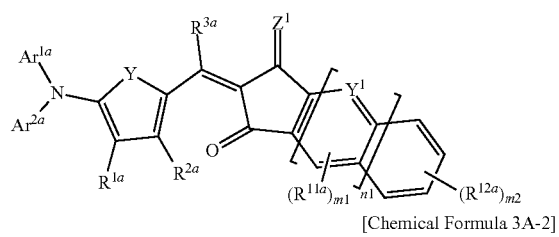

[Chemical Formula 3A-1]

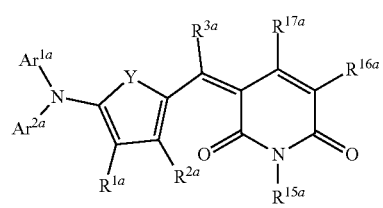

[Chemical Formula 3A-2]

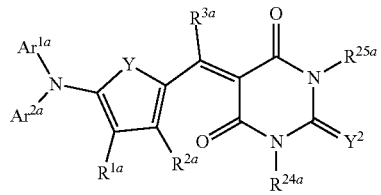

[Chemical Formula 3A-3]

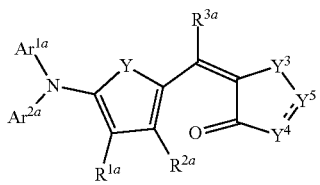

[Chemical Formula 3A-4]

In Chemical Formulas 3A-1 to 3A-4,

Y is Se, Te, S, SO, SO$_2$, or SiR$^h$R$^i$,

Z$^1$ is O or CR$^q$R$^r$,

Y$^1$ is N or CR$^s$,

Y$^2$ is one of O, S, Se, Te, and C(R$^t$)(CN),

Y$^3$ is O, S, Se, or Te,

Y$^4$ is N or NR$^{18a}$,

Y$^5$ is CR$^{19}$a or C=CR$^{20a}$(CN),

Ar$^{1a}$ and Ar$^{2a}$ are independently a substituted or unsubstituted C6 to C30 aryl group or a substituted or unsubstituted C3 to C30 heteroaryl group, wherein Ar$^{1a}$ and Ar$^{2a}$ are independently present or linked to each other to form a ring, R$^{1a}$ to R$^{3a}$, R$^{11a}$, R$^{12a}$, R$^{15a}$ to R$^{20a}$, R$^{24a}$, R$^{25a}$, R$^h$, R$^i$, and R$^q$ to R$^t$ are independently hydrogen, deuterium, a substituted or unsubstituted C1 to C30 an alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, n1 is 0 or 1, m1 is 0 or 1, and m2 is an integer ranging from 0 to 4.

The light absorbing material represented by one of Chemical Formulae 3A-1 to 3A-4 may be for example one of compounds of Groups 4 to 7, but is not limited thereto.

[Group 4]

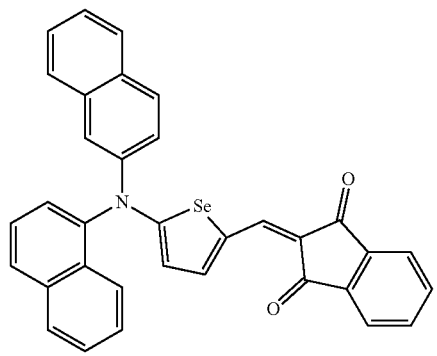

33
-continued
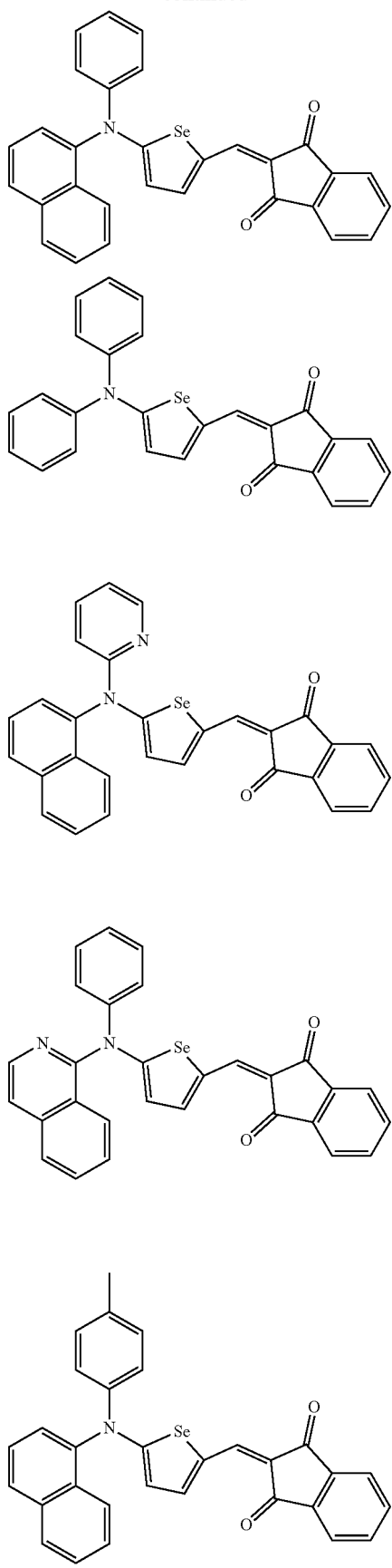
34
-continued
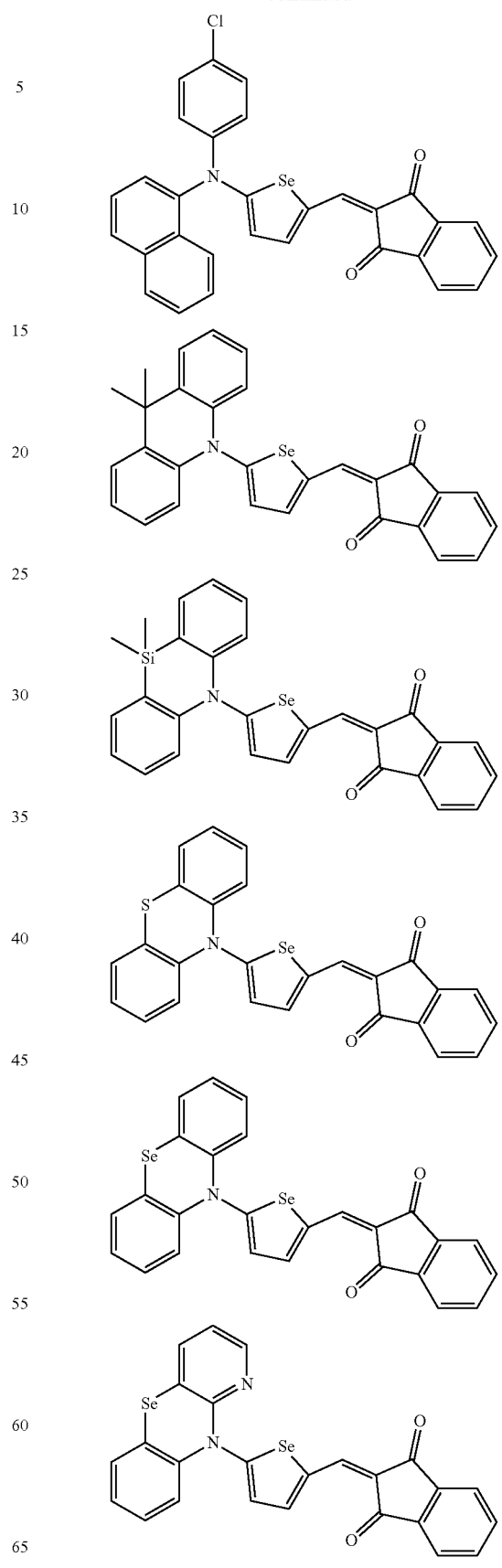

[Group 5]
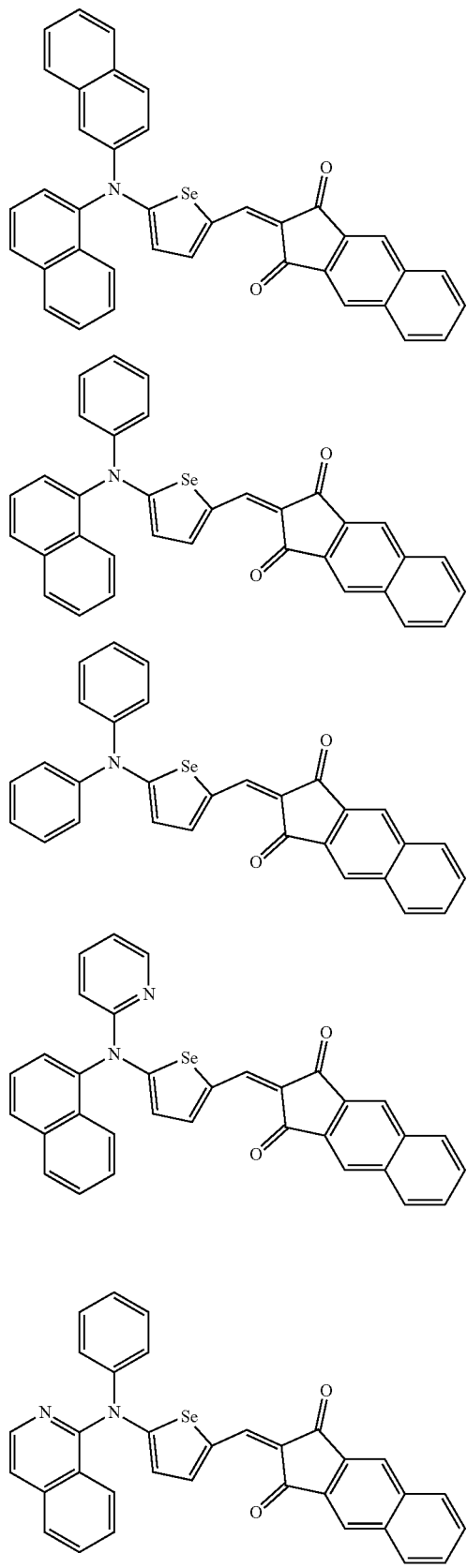
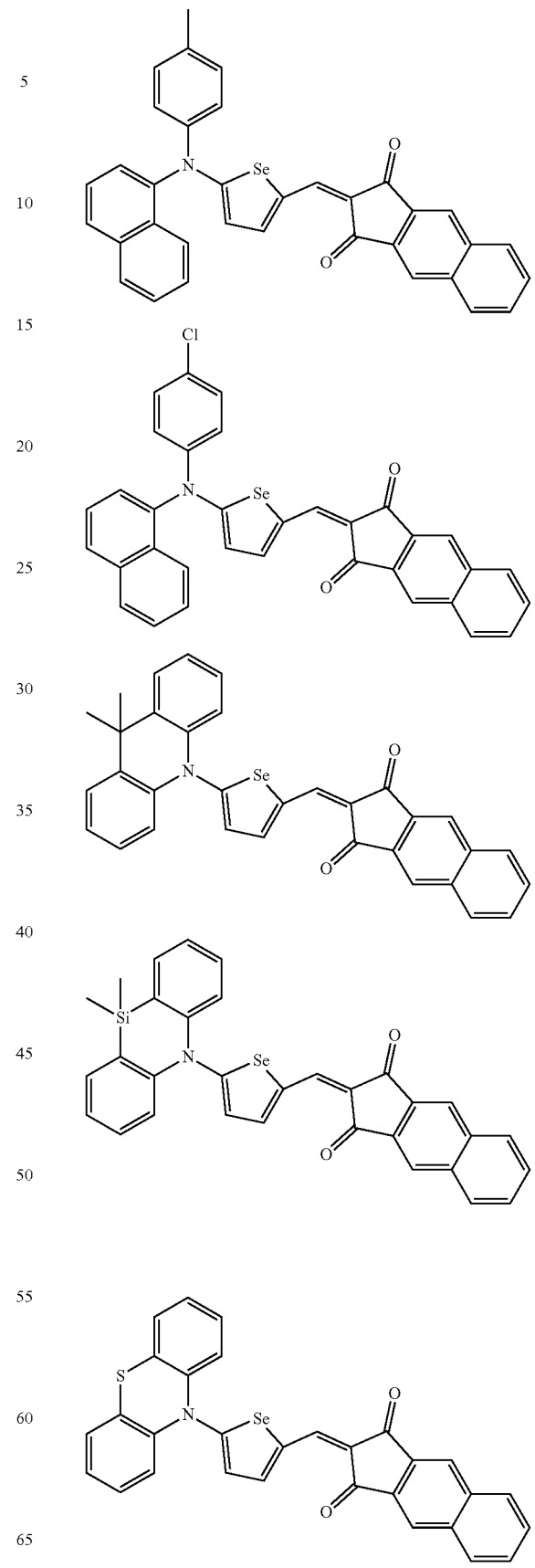

-continued
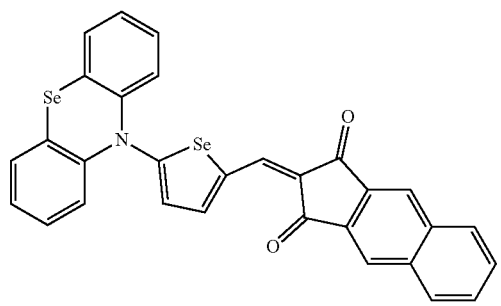
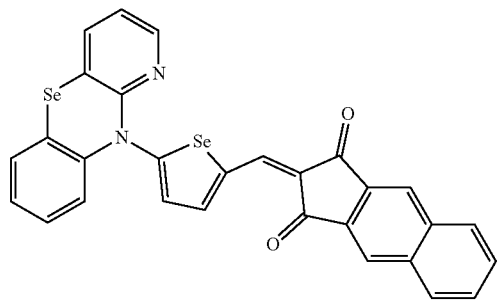
[Group 6]
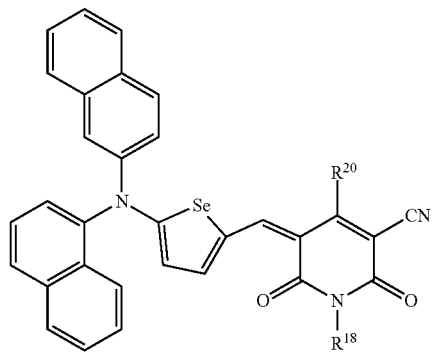
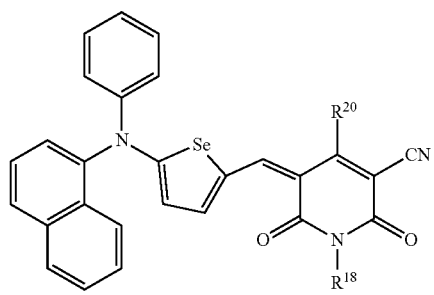
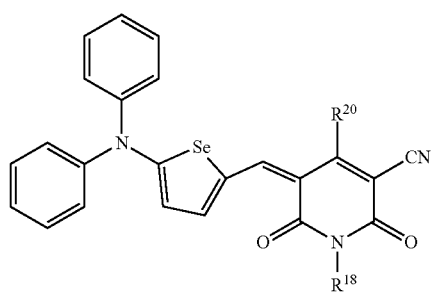
-continued
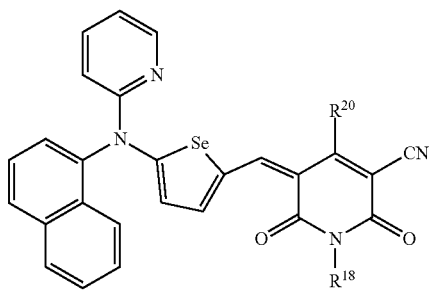
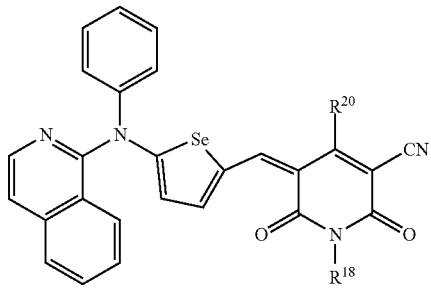
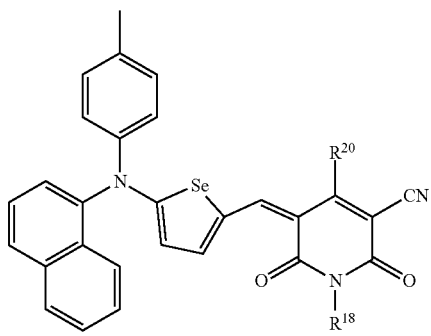
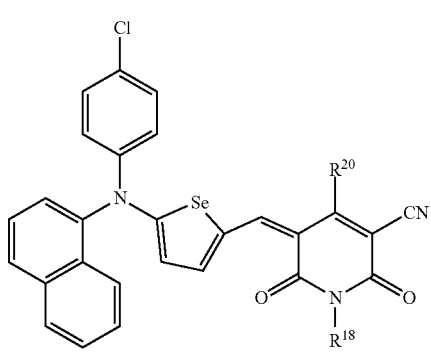
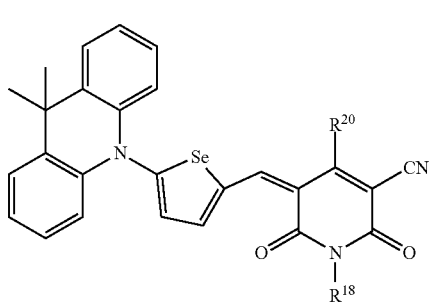

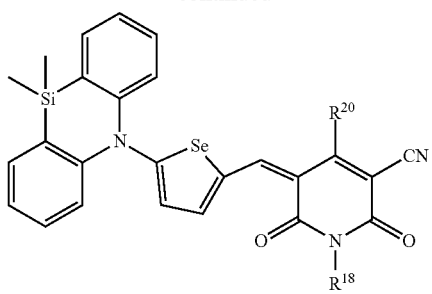
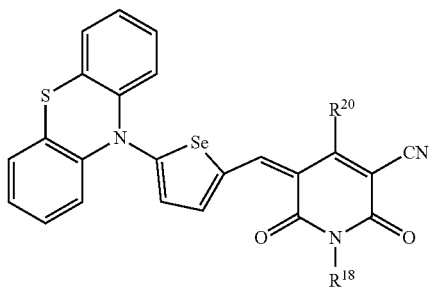
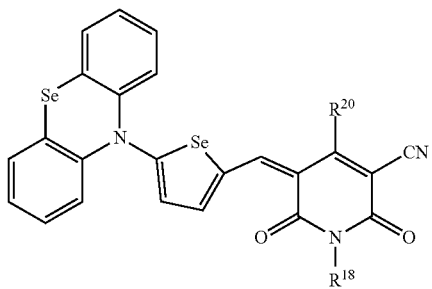
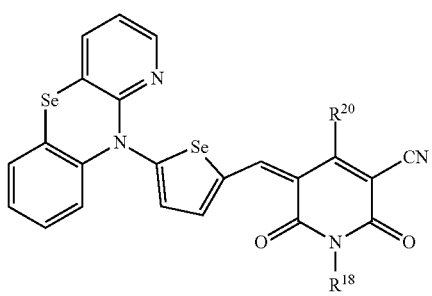
[Group 7]
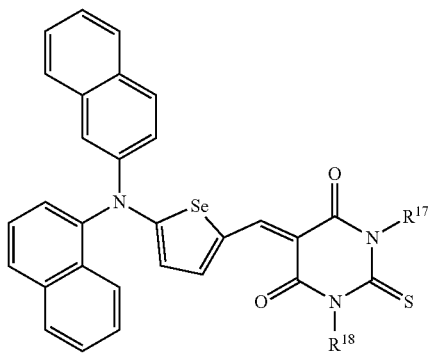
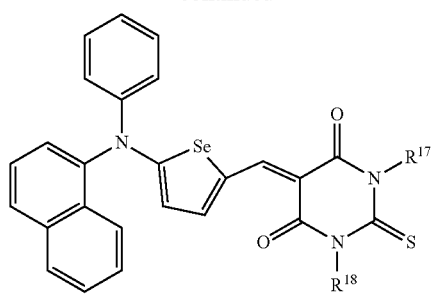
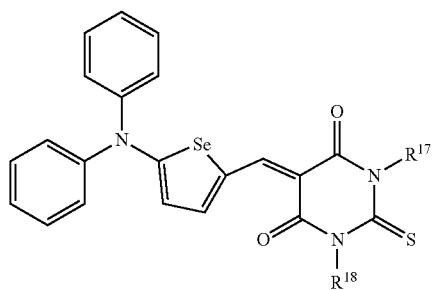
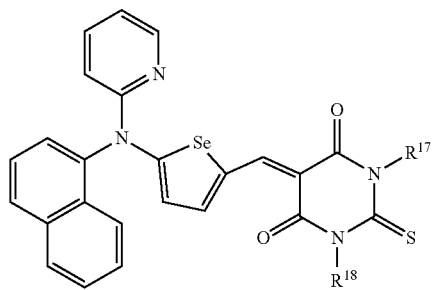
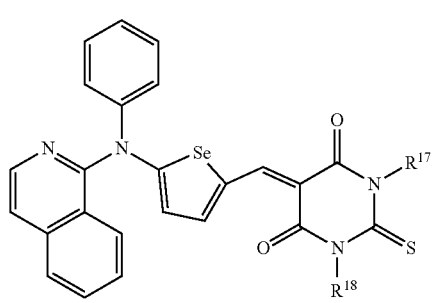
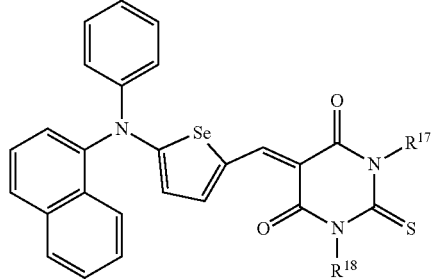

-continued

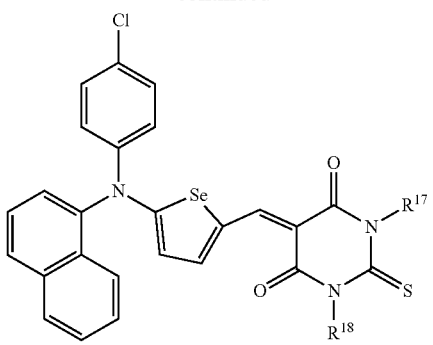
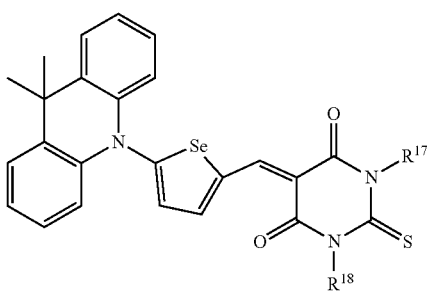
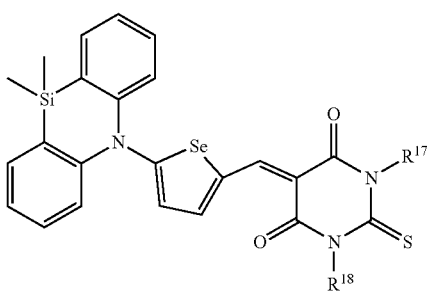
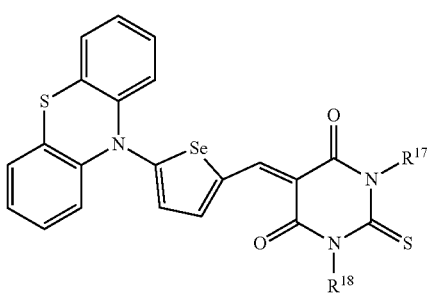
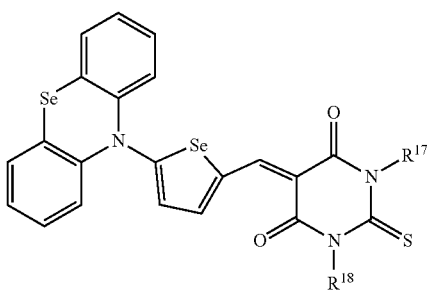

-continued

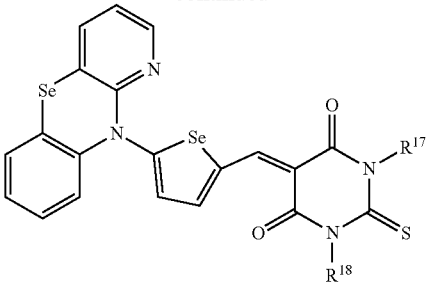

In Groups 4 to 7,
hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, and $R^{16}$, $R^{17}$, $R^{18}$, and $R^{20}$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof.

The n-type semiconductor may have a LUMO energy level, a HOMO energy level, and a bandgap energy which are effective for electrical matching with the aforementioned p-type semiconductor.

The p-type semiconductor and the n-type semiconductor may be formed into the active layer 30 by codeposition using sublimation.

For example, the active layer 30 including the compound represented by Chemical Formula 1, the compound represented by Chemical Formula 2, or the combination thereof as the n-type semiconductor may have different the light absorption characteristics from an active layer including unsubstituted fullerene (e.g., C60 fullerene) and the active layer 30 including the aforementioned compound may have reduced abnormal absorption in a short wavelength region of visible light, for example from about 400 nm to about 500 nm. For example, an absorption coefficient at the wavelength of 450 nm of the active layer 30 including the compound may be smaller than that of an active layer including unsubstituted fullerene (e.g., C60 fullerene), for example, the absorption coefficient at the wavelength of 450 nm of the active layer 30 including the compound represented by Chemical Formula 1 or Chemical Formula 2 may be, for example, less than or equal to about 75%, for example, less than or equal to about 50% of that of the active layer including unsubstituted fullerene (e.g., C60 fullerene).

The light absorption characteristics of the active layer 30 may be expressed by a combination of light absorption characteristics by the p-type semiconductor and light absorption characteristics by the n-type semiconductor composition. Accordingly, the active layer 30 including the p-type semiconductor selectively absorbing light in a wavelength region of about 500 nm to about 600 nm and the n-type semiconductor may increase wavelength selectivity due to easy separation of an absorption peak compared with the active layer including the p-type semiconductor selectively absorbing in a wavelength region of about 500 nm to about 600 nm and the unsubstituted fullerene (e.g., C60 fullerene). Accordingly, the former active layer may be effectively used for an organic photoelectric device requiring wavelength selectivity.

The active layer 30 may include an intrinsic layer formed by codepositing the aforementioned p-type semiconductor and n-type semiconductor. The p-type semiconductor and n-type semiconductor may be included in a volume ratio of about 1:9 to about 9:1, about 2:8 to about 8:2, about 3:7 to about 7:3, about 4:6 to about 6:4, or about 5:5.

The active layer 30 may further include a fullerene or a fullerene derivative in addition to the aforementioned p-type semiconductor and n-type semiconductor. In other words, the active layer 30 may include three components such as the p-type semiconductor, the first n-type semiconductor including the compound represented by Chemical Formula 1 or Chemical Formula 2, and the second n-type semiconductor including fullerene or fullerene derivative. When the active layer 30 further includes the fullerene or the fullerene derivative, the first n-type semiconductor may be used in an amount of less than about 50 volume %, for example, less than or equal to about 45 volume %, less than or equal to about 40 volume %, less than or equal to about 35 volume %, less than or equal to about 30 volume %, or less than or equal to about 25 volume % based on the total amount (100 volume %) of the first n-type semiconductor and the second n-type semiconductor. Within the ranges, unnecessary absorption in the blue region (about 400 nm to about 500 nm) may be decreased, and absorption in the green region may be increased.

The active layer 30 may further include a p-type layer and/or an n-type layer in addition to the intrinsic layer. The p-type layer may include the aforementioned p-type semiconductor and the n-type layer may include the aforementioned N-type semiconductor. For example, the active layer may include various combinations of a p-type layer/an I layer, an I layer/an n-type layer, a p-type layer/an I layer/an n-type layer, and the like.

The organic photoelectric device 100 may further include a charge auxiliary layer (not shown) between the first electrode 10 and the active layer 30 and/or between the second electrode 20 and the active layer 30.

The charge auxiliary layer may make holes and electrons separated in the active layer 30 be transported easily to improve efficiency.

The charge auxiliary layer may include at least one selected from a hole injection layer for facilitating hole injection, a hole transport layer for facilitating hole transport, an electron blocking layer for preventing electron transport, an electron injection layer for facilitating electron injection, an electron transport layer for facilitating electron transport, and a hole blocking layer for preventing hole transport.

The charge auxiliary layer may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layer may include the aforementioned n-type semiconductor.

The organic photoelectric device 100 may further include an anti-reflection layer (not shown) on one surface of the first electrode 10 or the second electrode 20. The anti-reflection layer is disposed at a light incidence side and lowers reflectance of light of incident light and thereby light absorbance is further improved. For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5, and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the organic photoelectric device 100, when light enters from the first electrode 10 or second electrode 20 and the active layer 30 absorbs light in a predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of the first electrode 10 and the second electrode 20 so as to flow a current.

The organic photoelectric device 100 may be applied to a solar cell, an image sensor, a photodetector, a photosensor, and an organic light emitting diode (OLED), but is not limited thereto.

The organic photoelectric device may be for example applied to an image sensor.

Hereinafter, an example of an image sensor including the photoelectric device is described referring to drawings. As an example of an image sensor, an organic CMOS image sensor is described.

Figure 2:
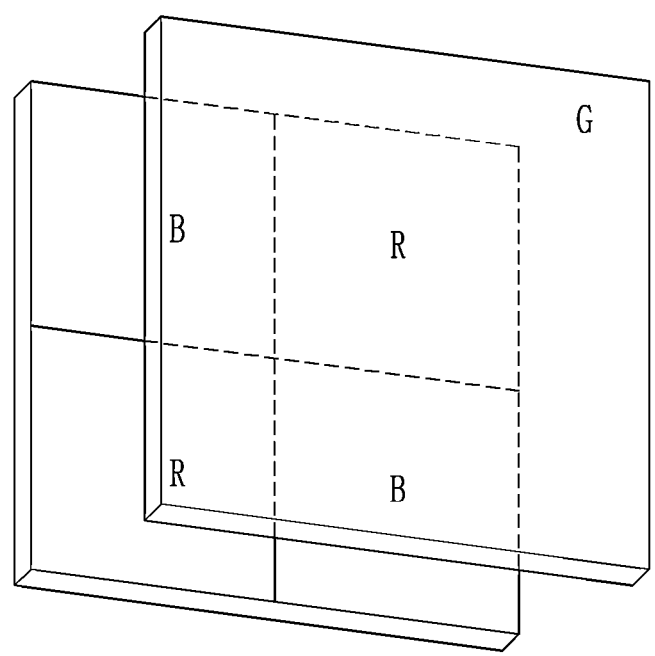
FIG. 2 is a plan view schematically illustrating a CMOS image sensor according to an embodiment.
Figure 3:
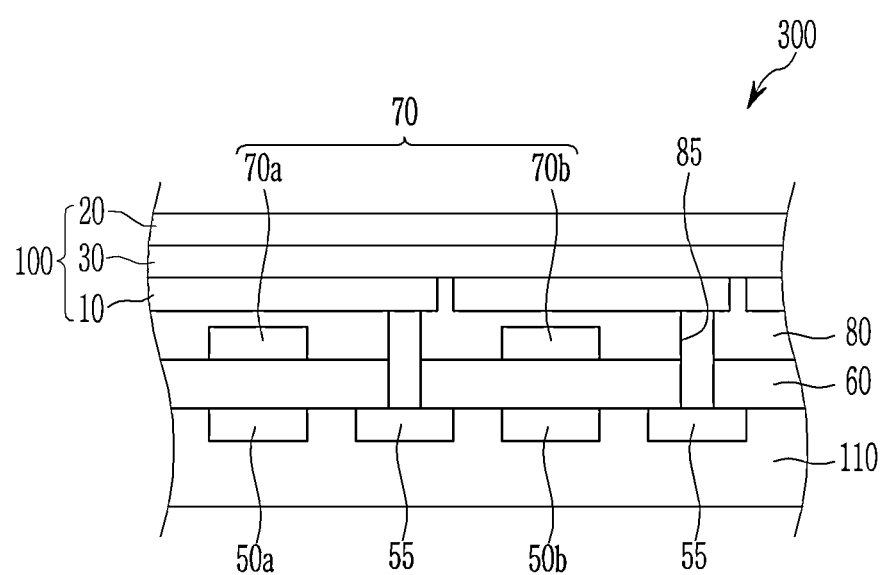
FIG. 3 is a cross-sectional view illustrating an example of the CMOS image sensor of FIG. 2.

FIG. 2 is a schematic top plan view of an organic CMOS image sensor according to an embodiment and FIG. 3 is a cross-sectional view showing one example of the organic CMOS image sensor of FIG. 2.

Referring to FIGS. 2 and 3, an organic CMOS image sensor 300 according to an example embodiment includes a semiconductor substrate 110 integrated with photo-sensing devices 50a and 50b, a transmission transistor (not shown) and a charge storage 55, a lower insulation layer 60, a color filter layer 70, an upper insulation layer 80, and an organic photoelectric device 100.

The semiconductor substrate 110 may be a silicon substrate, and is integrated with the photo-sensing devices 50a and 50b, the transmission transistor (not shown), and the charge storage 55. The photo-sensing devices 50a and 50b may be photodiodes.

The photo-sensing devices 50a and 50b, the transmission transistor, and/or the charge storage 55 may be integrated in each pixel, and as shown in the drawing, the photo-sensing devices 50a and 50b may be respectively included in a blue pixel and a red pixel and the charge storage 55 may be included in a green pixel.

The photo-sensing devices 50a and 50b sense light, the information sensed by the photo-sensing devices may be transferred by the transmission transistor, the charge storage 55 is electrically connected to the organic photoelectric device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing device 50*a* and 50*b*.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70*a* formed in a blue pixel and a red filter 70*b* in a red pixel. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned organic photoelectric device 100 is formed on the upper insulation layer 80. The organic photoelectric device 100 includes the first electrode 10, the active layer 30, and the second electrode 20 as described above. In the drawing, the first electrode 10, the active layer 30, and the second electrode 20 are sequentially stacked, but this disclosure is not limited thereto, and for example they may be stacked in an order of the second electrode 20, the active layer 30, and the first electrode 10.

The first electrode 10 and the second electrode 20 may be all light-transmitting electrodes and the active layer 30 is the same as described above. The active layer 30 may for example selectively absorb light in a green wavelength region and may replace a color filter of a green pixel.

Light in a green wavelength region of light that enters from the second electrode 20 is mainly absorbed by the active layer 30 and photoelectrically converted and light in a remaining wavelength region is transmitted through the first electrode 10 and is sensed by the photo-sensing devices 50*a* and 50*b*.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device 100 has a stack structure thereby a size of an image sensor may be reduced to realize a down-sized image sensor.

In addition, the active layer 30 includes the fullerene derivative having optical absorption characteristics shifted toward a short wavelength as described above and thus may increase wavelength selectivity compared with the one including the unsubstituted C60 fullerene.

The organic photoelectric device selectively absorbing light in a green wavelength region is for example stacked but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a green photo-sensing device and a blue photo-sensing device may be integrated in the semiconductor substrate 110.

Figure 4:
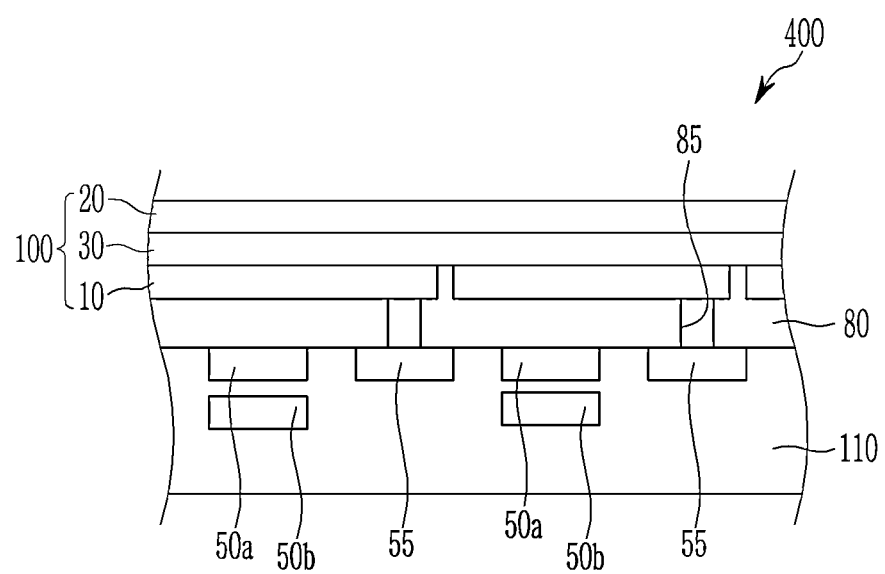
FIG. 4 is a cross-sectional view showing another example of a CMOS image sensor.

FIG. 4 is a cross-sectional view showing another example of the organic CMOS image sensor.

The organic CMOS image sensor 400 according to the present embodiment like the above embodiment includes a semiconductor substrate 110 integrated with photo-sensing devices 50*a* and 50*b*, a transmission transistor (not shown), and a charge storage 55, an upper insulation layer 80 having a through-hole 85, and an organic photoelectric device 100.

However, in the CMOS image sensor 400 according to the present embodiment unlike the above embodiment, the photo-sensing devices 50*a* and 50*b* are stacked in a vertical direction, but the color filter layer 70 is omitted. The photo-sensing devices 50*a* and 50*b* are electrically connected to charge storage (not shown) and may be transferred by the transmission transistor. The photo-sensing devices 50*a* and 50*b* may selectively absorb light in each wavelength region depending on a stacking depth.

Focusing lens (not shown) may be further formed on the organic photoelectric device 100. The focusing lens may control a direction of incident light and gather the light in one region. The focusing lens may have a shape of, for example, a cylinder or a hemisphere, but is not limited thereto.

As described above, the organic photoelectric device selectively absorbing light in a green wavelength region is stacked and the red photo-sensing device and the blue photo-sensing device are stacked, and thereby a size of an image sensor may be reduced to realize a down-sized image sensor.

In FIG. 4, the organic photoelectric device selectively absorbing light in a green wavelength region is for example stacked, but this disclosure is not limited thereto. For example, an organic photoelectric device selectively absorbing light in a blue wavelength region may be stacked and a green photo-sensing device and a red photo-sensing device may be integrated in the semiconductor substrate 110 or an organic photoelectric device selectively absorbing light in a red wavelength region may be stacked and a green photo-sensing device and a blue photo-sensing device may be integrated in the semiconductor substrate 110.

Figure 5:
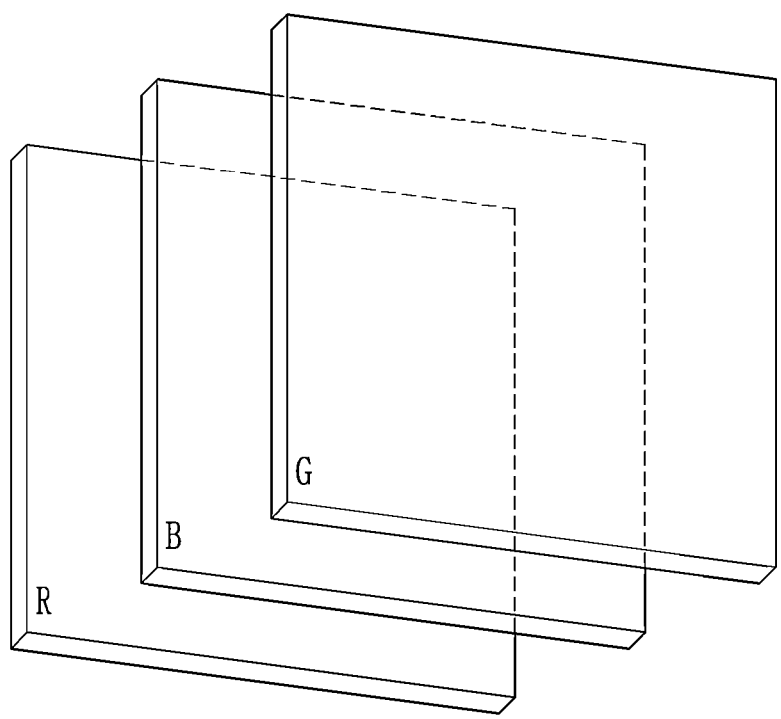
FIG. 5 is a plan view schematically illustrating a CMOS image sensor according to another embodiment.
Figure 6:
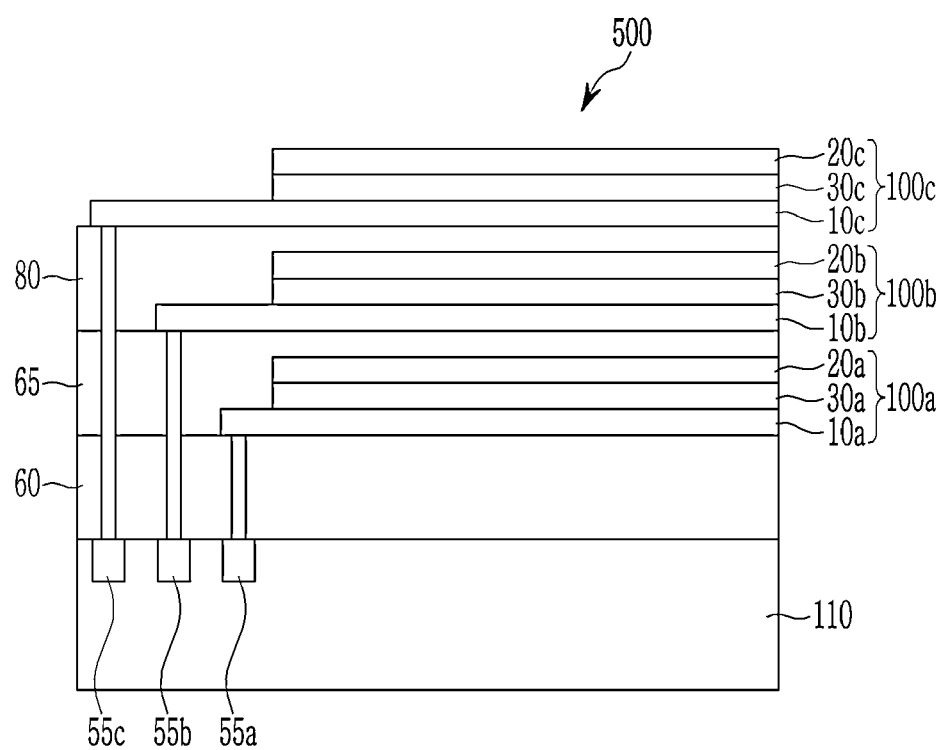
FIG. 6 is a cross-sectional view of the CMOS image sensor of FIG. 5, and FIGS. 7 and 8 are optical micrographs of thin films including the compounds of Synthesis Examples 4 and 5, respectively.

FIG. 5 is a schematic top plan view showing an organic CMOS image sensor according to another embodiment and FIG. 6 is a cross-sectional view of the organic CMOS image sensor of FIG. 5.

The organic CMOS image sensor 500 according to the present embodiment includes a green organic photoelectric device selectively absorbing light in a green wavelength region, a blue organic photoelectric device selectively absorbing light in a blue wavelength region, and a red organic photoelectric device selectively absorbing light in a red wavelength region that are stacked.

The organic CMOS image sensor 500 according to the present embodiment includes a semiconductor substrate 110, a lower insulation layer 60, an intermediate insulation layer 65, an upper insulation layer 80, a first organic photoelectric device 100*a*, a second organic photoelectric device 100*b*, and a third organic photoelectric device 100*c*.

The semiconductor substrate 110 may be a silicon substrate, and is integrated with the transmission transistor (not shown) and the charge storages 55a, 55b, and 55c.

A metal wire (not shown) and pad (not shown) are formed on the semiconductor substrate 110 and a lower insulation layer 60 is formed on the metal wire and pad.

The first organic photoelectric device 100a is formed on the lower insulation layer 60.

The first organic photoelectric device 100a includes a first electrode 10a and a second electrode 20a facing each other and an active layer 30a disposed between the first electrode 10a and the second electrode 20a. The first electrode 10a, the second electrode 20a, and the active layer 30a are the same as described above and the active layer 30a may selectively absorb light in one wavelength region of red, blue, and green. For example, the first organic photoelectric device 100a may be a red organic photoelectric device.

In the drawing, the first electrode 10a, the active layer 30a, and the second electrode 20a are sequentially stacked, but this disclosure is not limited thereto, and for example they may be stacked in an order of the second electrode 20a, the active layer 30a, and the first electrode 10a.

The intermediate insulation layer 65 is formed on the first organic photoelectric device 100a.

The second organic photoelectric device 100b is formed on the intermediate insulation layer 65.

The second organic photoelectric device 100b includes a first electrode 10b and a second electrode 20b facing each other and an active layer 30b disposed between the first electrode 10b and the second electrode 20b. The first electrode 10b, the second electrode 20b, and the active layer 30b are the same as described above and the active layer 30b may selectively absorb light in one wavelength region of red, blue and green. For example, the second photoelectric device 100b may be a blue organic photoelectric device.

In the drawing, the first electrode 10b, the active layer 30b, and the second electrode 20b are sequentially stacked, but this disclosure is not limited thereto, and for example they may be stacked in an order of the second electrode 20b, the active layer 30b, and the first electrode 10b.

The upper insulation layer 80 is formed on the second organic photoelectric device 100b. The lower insulation layer 60, the intermediate insulation layer 65, and the upper insulation layer 80 have a plurality of through-holes exposing the charge storages 55a, 55b, and 55c.

The third organic photoelectric device 100c is formed on the upper insulation layer 80. The third organic photoelectric device 100c includes a first electrode 10c and a second electrode 20c facing each other and an active layer 30c disposed between the first electrode 10c and the second electrode 20c. The first electrode 10c, the second electrode 20c, and the active layer 30c are the same as described above and the active layer 30c may selectively absorb light in one wavelength region of red, blue, and green. For example, the third organic photoelectric device 100c may be a green organic photoelectric device.

In the drawing, the first electrode 10c, the active layer 30c, and the second electrode 20c are sequentially stacked, but this disclosure is not limited thereto, and for example they may be stacked in an order of the second electrode 20c, the active layer 30c, and the first electrode 10c.

Focusing lens (not shown) may be further formed on the organic photoelectric device 100c. The focusing lens may control a direction of incident light and gather the light in one region. The focusing lens may have a shape of, for example, a cylinder or a hemisphere, but is not limited thereto.

In the drawing, the first organic photoelectric device 100a, the second organic photoelectric device 100b, and the third organic photoelectric device 100c are sequentially stacked, but the present disclosure is not limited thereto, and they may be stacked in various orders.

As described above, the first organic photoelectric device 100a, the second organic photoelectric device 100b, and the third organic photoelectric device 100c that absorb light in different wavelength regions are stacked, and thereby a size of an image sensor may be reduced to realize a down-sized image sensor.

The image sensor may be applied to, for example, various electronic devices such as a mobile phone or a digital camera, but is not limited thereto.

Hereinafter, the embodiments are illustrated in more detail with reference to examples. However, these examples are non-limiting examples, and the scope of claims is not limited thereto.

Synthesis Example: Synthesis of N-Type Semiconductor

Synthesis Example 1: Synthesis of (2Z,2'Z,2"Z)-3, 3',3"-(benzene-1,3,5-triyl)tris(2-(3,4-dichlorophenyl) acrylonitrile

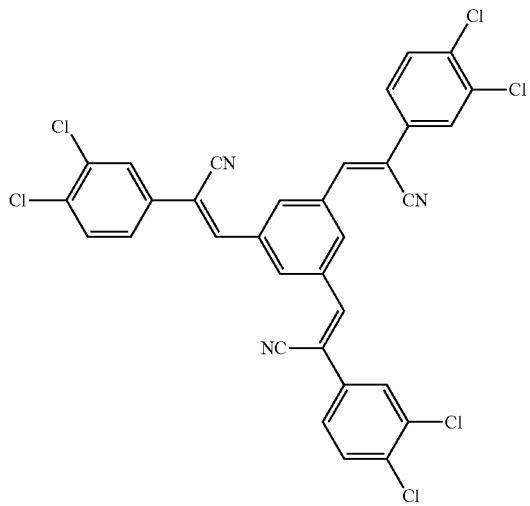

[Chemical Formula A]

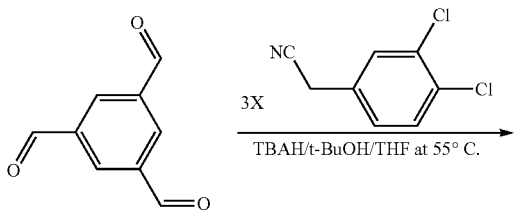

[Reaction Scheme A]

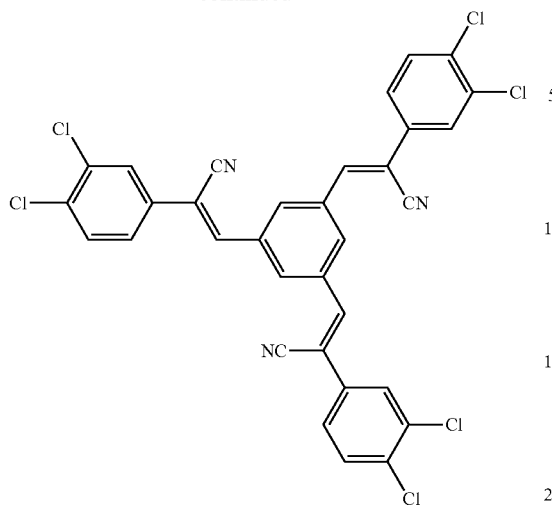

A mixture of benzene-1,3,5-tricarbaldehyde (1 eq.) and 2-(3,4-dichlorophenyl)acetonitrile (3.3 eq.) is dissolved in a mixed solvent of t-butanol (t-BuOH) and tetrahydrofuran (THF) and then, put in a round-bottomed flask and stirred at 55° C. Tetrabutylammonium hydroxide (TBAH, a 1 M solution in methanol (MeOH), 0.33 eq.) is added thereto and then, stirred for 1 hour. After decreasing a temperature thereof to room temperature, MeOH is added thereto to precipitate a product, and the product is filtered to obtain a powder product. The powder is several times washed with methanol and recrystallized with an MeOH solvent for purification. The obtained product is dried in an 80° C. vacuum oven for 24 hours.

1H NMR (300 MHz, CDCl$_3$): δ=8.41 (s, 3H), 7.82 (s, 3H), 7.62 (s, 3H), 7.57 (s, 6H).

Synthesis Example 2: Synthesis of (2Z,2'Z,2''Z)-3,3',3''-(benzene-1,3,5-triyl)tris(2-(pyridin-2-yl)acrylonitrile)

[Chemical Formula B]

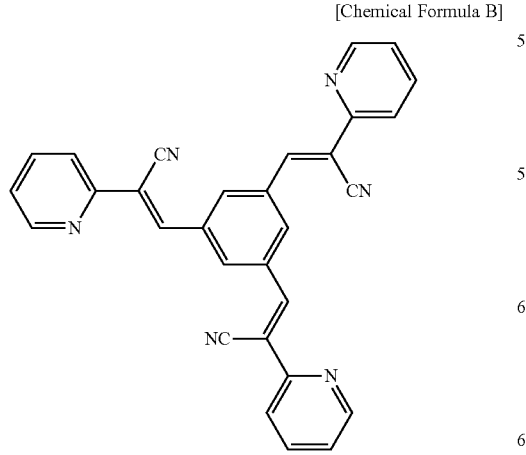

[Reaction Scheme B]

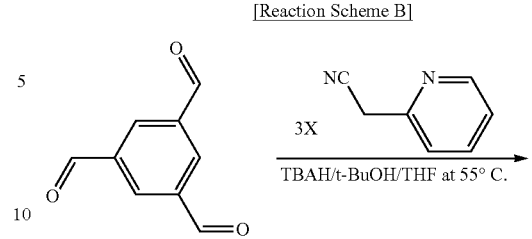

A mixture of benzene-1,3,5-tricarbaldehyde (1 eq.) and 2-(pyridin-2-yl)acetonitrile (3.3 eq.) is dissolved in a mixed solvent of t-BuOH and THF in a round-bottomed flask and then, stirred at 55° C. Tetrabutylammonium hydroxide (TBAH, a 1 M solution in MeOH) (0.33 eq.) is added thereto and then, stirred for one hour mixture. After decreasing a temperature thereof to room temperature, MeOH is added thereto to precipitate a product, and the product is filtered to obtain a powder product. The powder product is several times washed with methanol and recrystallized with a MeOH solvent for purification. The obtained product is dried in an 80° C. oven for 24 hours.

$^1$H NMR (300 MHz, CDCl$_3$): δ=8.69 (dt, 3H), 8.61 (s, 3H), 8.59 (s, 3H), 7.83 (m, 6H), 7.34 (m, 6H).

Synthesis Example 3: Synthesis of 2,4,6-tri(pyridin-4-yl)-1,3,5-triazine

[Chemical Formula C]

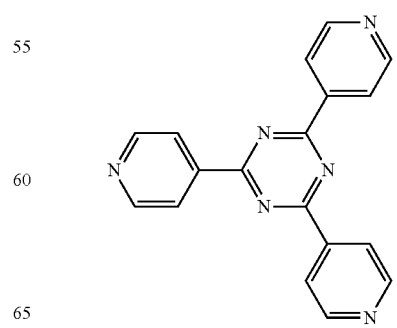

[Reaction Scheme C]

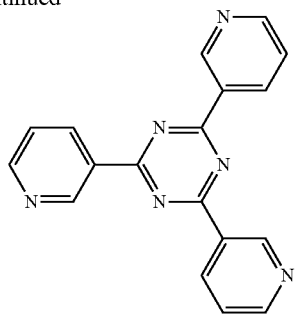

Isonicotinonitrile (1 eq.) is heated at 150° C. into liquid, and NaOH (0.1 eq.) is added thereto and then, stirred for 24 hours. After decreasing a temperature thereof to room temperature, powder produced therein is several times washed with acetone. The obtained powder is dissolved in 2M HCl and then, treated with an $NH_3$ aqueous solution for precipitation and filtered. The obtained product is washed with water and acetone and then, dried in an 80° C. vacuum oven for 24 hours.

$^1$H NMR (300 MHz, DMSO-d6): δ=8.99 (d, 6H), 8.70 (d, 6H).

Synthesis Example 4: Synthesis of 2,4,6-tri(pyridin-3-yl)-1,3,5-triazine

[Chemical Formula D]

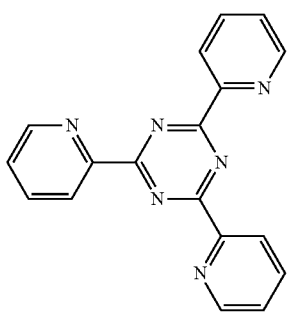

[Reaction Scheme D]

Nicotinonitrile (1 eq.) is heated at 150° C. into liquid, and NaOH (0.1 eq.) is added thereto and then, stirred for 24 hours. After decreasing a temperature thereof to room temperature, powder obtained therefrom is several times washed with acetone. The powder is dissolved in 2M HCl, treated with an $NH_3$ aqueous solution for precipitation, and filtered. The obtained product is washed with water and acetone and then, dried in an 80° C. vacuum oven for 24 hours.

$^1$H NMR (300 MHz, CDCl$_3$): δ=9.93 (s, 3H), 8.97 (d, 3H), 8.88 (d, 3H), 7.55 (dd, 3H).

Synthesis Example 5: Synthesis of 2,4,6-tri(pyridin-2-yl)-1,3,5-triazine

[Chemical Formula E]

[Reaction Scheme E]

Picolinonitrile (1 eq.) is heated at 150° C. into liquid, and NaOH (0.1 eq.) is added thereto and then, stirred for 24 hours. After decreasing a temperature thereof to room temperature, powder produced therein is several times washed with acetone. The obtained powder is dissolved in 2M HCl and then, treated with an NH₃ aqueous solution and filtered. The filtered product is washed with water and acetone and then, dried in an 80° C. vacuum oven for 24 hours.

¹H NMR (300 MHz, CDCl₃): δ=8.97 (d, 3H), 8.65 (d, 3H), 7.96 (t, 3H), 7.54 (m, 3H).

Synthesis Example 6: Synthesis of 2,5,8-triethyl-9-methylene-8,9-dihydro-1H-dipyrrolo[3,4-e:3',4'-g]isoindole-1,3,4,6,7(2H,5H)-pentaone

[Chemical Formula F]

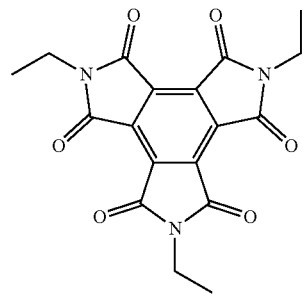

[Reaction Scheme F]

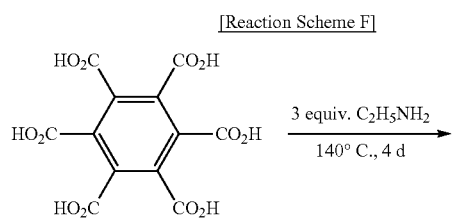

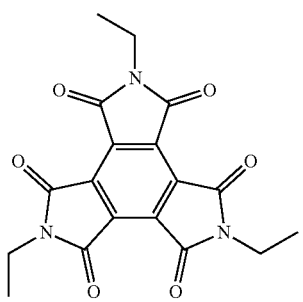

N-ethylamine (3 eq.) is dissolved in a mellitic acid (1 eq.) aqueous solution and then, put in a round-bottomed flask and stirred at 140° C. for 4 days. After decreasing a temperature thereof to room temperature, the resultant is extracted and then, silica column-purified. The obtained product is dried in an 80° C. vacuum oven for 24 hours.

¹H NMR (300 MHz, CDCl₃): δ=3.88 (q, 6H), 1.33 (t, 9H).

Comparative Synthesis Example 1: C60 Fullerene

[Chemical Formula G]

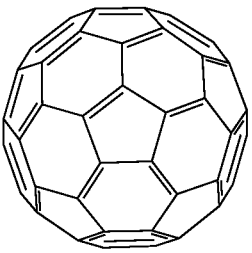

C60 fullerene (tradename: nanom purple ST, Frontier Carbon Corp.) is used.

Evaluation 1: Light Absorption Characteristics of Compounds

Reorganization energy and energy levels (HOMO, LUMO) of the compounds according to Synthesis Examples 1 to 6 and Comparative Synthesis Example 1 are evaluated, and the results are shown in Table 1. The reorganization energy is measured in a DFT B3LYP/6-311G(d,p) level by using a Gaussian 09 program to evaluate charge mobility. In addition, an AC-3 photoelectron spectrophotometer (RIKEN KEIKI) is used to measure HOMO's, and LUMO's are calculated by first obtaining bandgaps with Cary 5000 UV spectroscopy (Varian Medical Systems Inc.) and using them. The results are shown in Table 1.

TABLE 1

| | Reorganization energy (eV) | HOMO (eV) | LUMO (eV) |
|---|---|---|---|
| Synthesis Example 1 | 0.271 | −6.89 | −3.19 |
| Synthesis Example 2 | 0.229 | −6.51 | −2.74 |
| Synthesis Example 3 | 0.136 | −6.40 | −3.66 |
| Synthesis Example 4 | 0.248 | −7.26 | −2.54 |
| Synthesis Example 5 | 0.229 | −6.89 | −2.20 |
| Synthesis Example 6 | 0.291 | −6.19 | −3.09 |
| Comparative Synthesis Example 1 | 0.313 | −7.42 | −2.87 |

Referring to Table 1, the compounds according to Synthesis Examples 1 to 6 exhibit lower reorganization energy than the compound of Comparative Synthesis Example 1. Accordingly, the compounds of Synthesis Examples 1 to 6 turn out to have improved charge mobility, molecular stability, and packing properties during the deposition. In addition, the HOMO and LUMO energy levels of the compounds according to Synthesis Examples 1 to 6 exhibit that the compounds may be appropriately used as an n-type semiconductor.

Evaluation 2: Thermal Stability of Compounds

Figure 7:
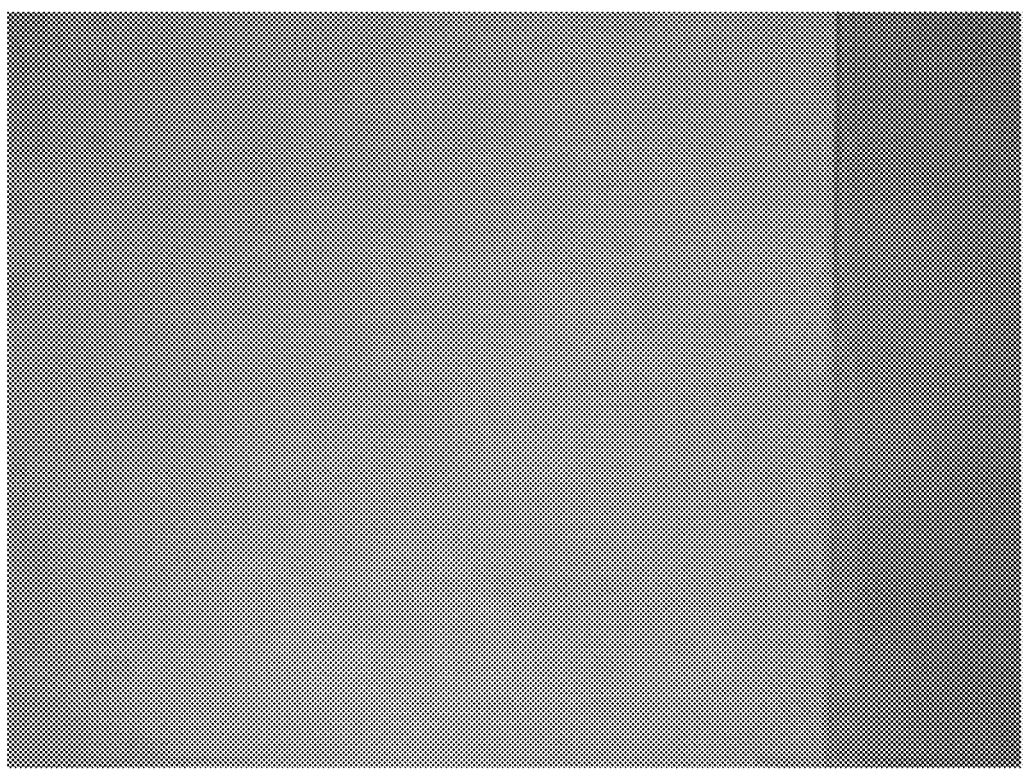
Figure 8:
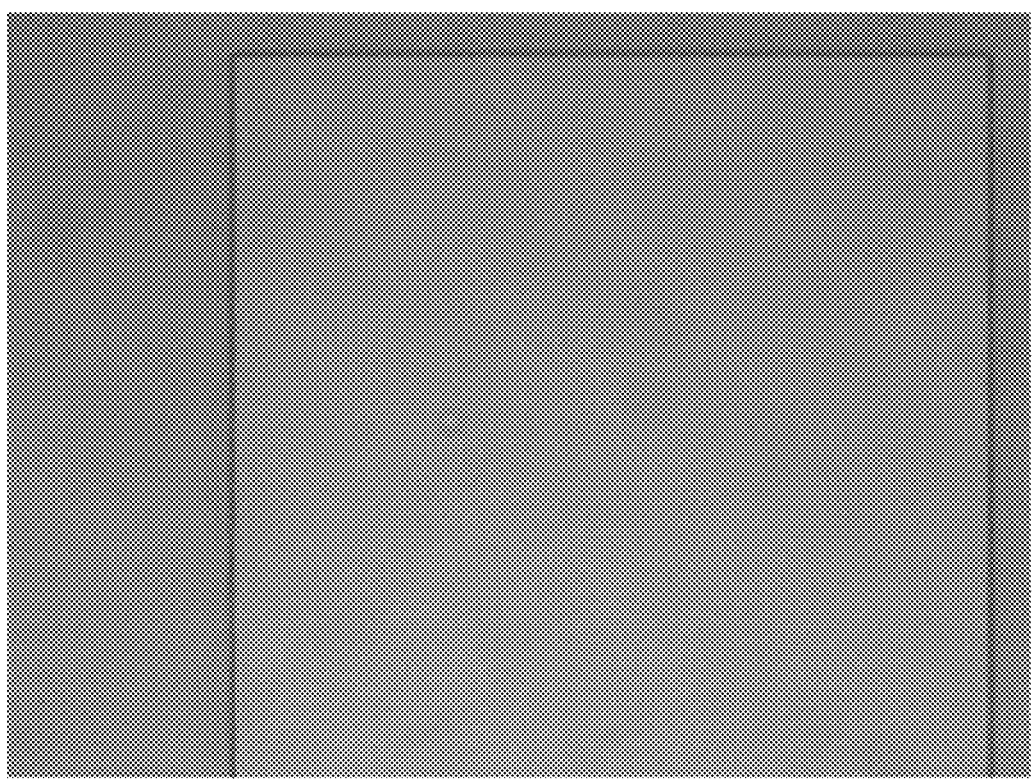

The compounds according to Synthesis Examples 1 to 6 are respectively formed into thin films through vacuum thermal deposition and then, allowed to stand at 160° C. for 3 hours. Optical micrographs of the thins films including the compounds of Synthesis Examples 4 and 5 are shown in FIGS. 7 and 8. FIGS. 7 and 8 respectively show optical micrographs of the thin films including the compounds of Synthesis Examples 4 and 5. Referring to FIGS. 7 and 8, the thin films including the compounds according to Synthesis Examples 4 and 5 exhibit no phase change after allowed to stand at a high temperature.

Example 1-1: Production of Organic Photoelectric Device

ITO is sputtered on a glass substrate to form an about 150 nm-thick anode, and then, an n-type semiconductor including the compound represented by Chemical Formula A according to Synthesis Example 1 and a p-type semiconductor including a compound represented by Chemical Formula X are codeposited to form a 100 nm-thick active layer. The n-type semiconductor and the p-type semiconductor are used in a volume ratio of 1:1.2. A charge auxiliary layer is formed thereon by depositing molybdenum oxide (MoOx, 0<x≤3) into a 10 nm-thick thin film. Subsequently, on the molybdenum oxide thin film, ITO is sputtered to form a 7 nm-thick cathode and thus manufacture an organic photoelectric device.

[Chemical Formula X]

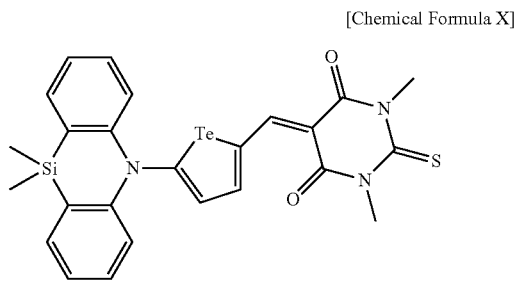

Examples 1-2 to 1-6 and Comparative Example 1-1: Production of Organic Photoelectric Devices Organic photoelectric devices are manufactured according to the same method as Example 1-1 except that the compounds according to Synthesis Examples 2 to 6 and Comparative Synthesis Example 1 are respectively used instead of the compound represented by Chemical Formula A according to Synthesis Example 1.

Example 2-1: Production of Organic Photoelectric Device

ITO is sputtered on a glass substrate to form an about 150 nm-thick anode, and then, an n-type semiconductor including the compound represented by Chemical Formula A according to Synthesis Example 1 and C60 fullerene represented by Chemical Formula G and a p-type semiconductor including the compound represented by Chemical Formula X are codeposited to form a 100 nm-thick active layer. The n-type semiconductor and p-type semiconductor compounds are used in a volume ratio of 1:1, and the compound represented by Chemical Formula A and C60 fullerene are used in a volume ratio of 25:75. Then, a charge auxiliary layer is formed thereon by depositing molybdenum oxide (MoOx, 0<x≤3) into a 10 nm-thick thin film. Subsequently, on the molybdenum oxide thin film, ITO is sputtered to form a 7 nm-thick cathode and thus manufacture an organic photoelectric device.

Examples 2-2 to 2-6 and Comparative Example 2-1: Production of Organic Photoelectric Device Organic photoelectric devices are manufactured according to the same method as Example 2-1 except that the compounds according to Synthesis Example 2 to 6 and Comparative Synthesis Example 1 are respectively used instead of the compound represented by Chemical Formula A according to Synthesis Example 1. Examples 3-1 to 3-6 and Comparative Example 3-1: Production of Organic CMOS Image Sensor (OCIS)

As the organic photoelectric device 100 of the image sensor 300 having the structure shown in FIG. 3, the organic photoelectric devices of Examples 1-1 to 1-6 and Comparative Example 1-1 are respectively disposed to manufacture image sensors.

Examples 4-1 to 4-6 and Comparative Example 4-1: Production of Organic CMOS Image Sensors (OCIS)

As the organic photoelectric device 100 of the image sensor 300 having the structure shown in FIG. 3, the organic photoelectric devices of Examples 2-1 to 2-6 and Comparative Example 2-1 are respectively disposed to manufacture image sensors.

Evaluation 3: External Quantum Efficiency of Organic Photoelectric Devices

External quantum efficiency (EQE) of the organic photoelectric devices according to Examples 1-1 to 2-6 and Comparative Examples 1-1 and 2-1 is measured. The external quantum efficiency is measured by using an IPCE measurement system (McScience Inc., Korea). First, the system is calibrated by using an Si photodiode (Hamamatsu Photonics K.K., Japan), and then, the organic photoelectric devices of Examples 1-1 to 2-6 and Comparative Examples 1-1 and 2-1 are mounted thereon to measure the external quantum efficiency in a wavelength range of about 400 nm to 700 nm. The external quantum efficiency (EQE, −3V) results at 450 nm of the organic photoelectric devices according to Examples 2-1 to 2-6 are shown in Table 2, and the external quantum efficiency (EQE, −3V) results at 550 thereof nm is shown in Table 3. The external quantum efficiency (EQE, −3V) result at 450 nm of the organic photoelectric device according to Comparative Example 2-1 is also measured for comparison and shown in Table 2.

TABLE 2

|  | EQE (450 nm) (%) |
| --- | --- |
| Example 2-1 | 8.5 |
| Example 2-2 | 8.5 |
| Example 2-3 | 9 |
| Example 2-4 | 8.7 |
| Example 2-5 | 9 |
| Example 2-6 | 11 |
| Comparative Example 2-1 | 20 |

TABLE 3

|  | EQE (550 nm) (%) |
| --- | --- |
| Example 2-1 | 49 |
| Example 2-2 | 45 |
| Example 2-3 | 46 |
| Example 2-4 | 44 |
| Example 2-5 | 45 |
| Example 2-6 | 50 |

Referring to Tables 2 and 3, the organic photoelectric devices according to Examples 2-1 to 2-6 exhibit a low light absorption in the blue region of 450 nm and a high light absorption in the green region of 550 nm.

While this disclosure has been described in connection with what is presently considered to be practical example embodiments, it is to be understood that the inventive concepts are not limited to the disclosed embodiments. On the contrary, inventive concepts are intended to cover various modifications and equivalent arrangements included within the spirit and scope of the appended claims.

DESCRIPTION OF SYMBOLS

100: organic photoelectric device
10: first electrode
20: second electrode
30: active layer
300, 400, 500: organic CMOS image sensor

What is claimed is:

1. An n-type semiconductor comprising a compound represented by Chemical Formula 2:

[Chemical Formula 2]

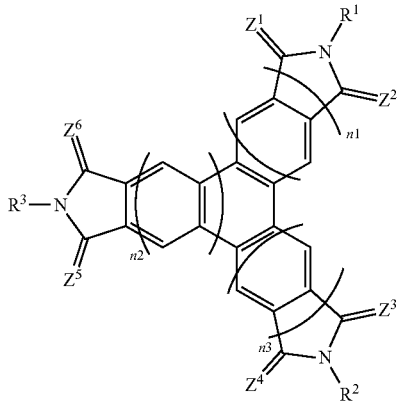

wherein, in Chemical Formula 2, $Z^1$ to $Z^6$ are independently O, S, Se, Te, or C(R)(CN), wherein R is hydrogen, deuterium, a cyano group (—CN), or a C1 to C10 alkyl group, $R^1$, $R^2$, and $R^3$ are independently hydrogen, deuterium, a halogen, a C1 to C10 alkyl group, a C1 to C10 haloalkyl group, a C2 to C10 heteroalkyl group, a C6 to C14 aryl group, or a C2 to C10 heteroaryl group, and n1, n2, and n3 are independently 0 or 1.

2. A thin film comprising:
the n-type semiconductor of claim 1.

3. An organic photoelectric device comprising:
a first electrode and a second electrode facing each other; and
an active layer between the first electrode and the second electrode,
the active layer including the n-type semiconductor of claim 1.

4. The organic photoelectric device of claim 3, wherein the active layer further comprises fullerene or a fullerene derivative.

5. An image sensor comprising:
the organic photoelectric device of claim 3.

6. An electronic device comprising
the organic photoelectric device of claim 4.

* * * * *